(12) United States Patent
Brandeis

(10) Patent No.: US 10,799,247 B2
(45) Date of Patent: Oct. 13, 2020

(54) VEIN ABLATION DEVICE

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 1018 days.

(21) Appl. No.: 15/028,970

(22) PCT Filed: Oct. 1, 2014

(86) PCT No.: PCT/IL2014/050863
§ 371 (c)(1),
(2) Date: Apr. 13, 2016

(87) PCT Pub. No.: WO2015/052703
PCT Pub. Date: Apr. 16, 2015

(65) Prior Publication Data
US 2016/0242790 A1    Aug. 25, 2016

Related U.S. Application Data

(60) Provisional application No. 61/890,269, filed on Oct. 13, 2013.

(51) Int. Cl.
*A61B 17/12* (2006.01)
*A61B 17/00* (2006.01)
(Continued)

(52) U.S. Cl.
CPC .. *A61B 17/12186* (2013.01); *A61B 17/00008* (2013.01); *A61B 17/12136* (2013.01);
(Continued)

(58) Field of Classification Search
CPC ........ A61B 17/12186; A61B 17/00008; A61B 17/32075; A61B 17/320758;
(Continued)

(56) References Cited

U.S. PATENT DOCUMENTS 5,492,535 A    2/1996    Reed et al.
5,868,708 A    2/1999    Hart et al.
(Continued)

FOREIGN PATENT DOCUMENTS

DE    3328530    2/1985
GB    526145    9/1940
(Continued)

OTHER PUBLICATIONS

Communication Relating to the Results of the Partial International Search dated Feb. 4, 2015 From the International Searching Authority Re. Application No. PCT/IL2014/050863.
(Continued)

*Primary Examiner* — Tiffany Legette

(57) ABSTRACT

An endovascular catheter for vein ablation comprising: an elongated rod sized for insertion into a vein; at least one irritation element coupled to the distal end portion of the rod, the at least one irritation element having an expanded irritation state for contacting an inner wall segment of the vein to irritate the vein segment to trigger spasm of the vein segment and a non-irritation state, the at least one irritation element arranged for iterative changes between the irritation state and the non-irritation state; and at least one support element coupled to the distal end portion of the rod, the support element arranged to apply a mechanical force from the distal end portion to iteratively return the irritation element to the expanded irritation state in response to dynamic feedback of vein walls pressing against the irritation element to force the irritation element into the non-irritation state.

6 Claims, 12 Drawing Sheets

(51) Int. Cl.
*A61B 17/3207* (2006.01)
*A61M 37/00* (2006.01)
*A61B 17/32* (2006.01)

(52) U.S. Cl.
CPC ............... *A61B 17/320725* (2013.01); *A61B 17/320758* (2013.01); *A61M 37/00* (2013.01); *A61B 2017/00893* (2013.01); *A61B 2017/320004* (2013.01); *A61B 2017/320064* (2013.01); *A61B 2017/320733* (2013.01)

(58) Field of Classification Search
CPC .. A61B 2017/2212; A61B 2017/22084; A61B 2017/22079; A61B 2017/12136; A61M 37/00; A71B 2017/00893; A71B 2017/320004; A71B 2017/320064; A71B 2017/320733
See application file for complete search history.

(56) References Cited

U.S. PATENT DOCUMENTS

| | | | |
|---|---|---|---|
| 6,962,576 | B2 | 11/2005 | Sibbitt |
| 8,177,740 | B1 | 5/2012 | McGlothlin et al. |
| 2001/0009989 | A1 | 7/2001 | Sibbitt |
| 2002/0010418 | A1 | 1/2002 | Lary et al. |
| 2002/0010487 | A1 | 1/2002 | Evans et al. |
| 2003/0069549 | A1 | 4/2003 | MacMahon et al. |
| 2003/0097114 | A1 | 5/2003 | Ouriel et al. |
| 2004/0004521 | A1 | 1/2004 | Hasegawa |
| 2006/0161103 | A1* | 7/2006 | Constantz ........... A61M 25/1011 604/101.04 |
| 2006/0184130 | A1 | 8/2006 | Sibbitt, Jr. et al. |
| 2007/0244429 | A1 | 10/2007 | Nguyen et al. |
| 2010/0042117 | A1 | 2/2010 | Kim et al. |
| 2011/0046543 | A1* | 2/2011 | Brandeis ........... A61B 17/00008 604/22 |
| 2011/0152683 | A1 | 6/2011 | Gerrans et al. |
| 2011/0152823 | A1* | 6/2011 | Mohiuddin ........... A61B 17/221 604/500 |
| 2012/0090620 | A1 | 4/2012 | Deutsch |
| 2013/0261538 | A1 | 10/2013 | Miyazaki et al. |
| 2016/0250143 | A1 | 9/2016 | Brandeis |
| 2016/0263319 | A1 | 9/2016 | Brandeis |

FOREIGN PATENT DOCUMENTS

| | | |
|---|---|---|
| WO | WO 2004/112569 | 12/2004 |
| WO | WO 2007/114934 | 10/2007 |
| WO | WO 2009/104189 | 8/2009 |
| WO | WO 2009/109967 | 9/2009 |
| WO | WO 2009/120432 | 10/2009 |
| WO | WO 2015/052702 | 4/2015 |
| WO | WO 2015/052703 | 4/2015 |
| WO | WO 2015/052704 | 4/2015 |

OTHER PUBLICATIONS

International Preliminary Report on Patentability dated Apr. 28, 2016 From the International Bureau of WIPO Re. Application No. PCT/IL2014/050862.
International Preliminary Report on Patentability dated Apr. 28, 2016 From the International Bureau of WIPO Re. Application No. PCT/IL2014/050863.
International Preliminary Report on Patentability dated Apr. 28, 2016 From the International Bureau of WIPO Re. Application No. PCT/IL2014/050864.
International Search Report and the Written Opinion dated Feb. 10, 2015 From the International Searching Authority Re. Application No. PCT/1L2014/050862.
International Search Report and the Written Opinion dated Feb. 23, 2015 From the International Searching Authority Re. Application No. PCT/IL2014/050863.
International Search Report and the Written Opinion dated Feb. 23, 2015 From the International Searching Authority Re. Application No. PCT/IL2014/050864.
Eckmann "Polidocanol for Endavenous Microfoam Sclerosant Therapy", Expert Opinion on Investigational Drugs, 18(2): 1919-1927, Dec. 2009.
Elias et al. "Mechanochemical Tumescentless Endovenous Ablation: Final Results of the Initial Clincal Trial", Phlebology, 27: 67-72, 2012.
Jones et al. "Management of Varicose Veins", American Family Physicians, 78(11): 1289-1294, 2008.
Subramonia et al. "The Treatment of Varicose Veins", Annals of The Royal College of Surgeons of England, 89(2): 96-100, Mar. 2007.
Restriction Official Action dated Jan. 29, 2018 From the US Patent and Trademark Office Re. U.S. Appl. No. 15/028,965. (8 pages).
Official Action dated May 25, 2018 From the US Patent and Trademark Office Re. U.S. Appl. No. 15/028,968. (18 pages).
Communication Pursuant to Article 94(3) EPC dated Sep. 16, 2019 From the European Patent Office Re. Application No. 14793315.4. (3 Pages).
Communication Pursuant to Article 94(3) EPC dated Dec. 4, 2018 From the European Patent Office Re. Application No. 14796554.5. (4 Pages).
Communication Pursuant to Article 94(3) EPC dated Feb. 28, 2019 From the European Patent Office Re. Application No. 14793315.4. (4 Pages).
Communication Pursuant to Article 94(3) EPC dated Jan. 31, 2018 From the European Patent Office Re. Application No. 14803252.7. (4 Pages).
Invitation Pursuant to Rule 137(4) EPC and Article 94(3) EPC dated Jun. 16, 2017 From the European Patent Office Re. Application No. 14803252.7. (1 Page).
Official Action dated Apr. 13, 2018 From the US Patent and Trademark Office Re. U.S. Appl. No. 15/028,965. (16 pages).
Communication Pursuant to Article 94(3) EPC dated Apr. 1, 2019 From the European Patent Office Re. Application No. 14803252.7. (5 Pages).

\* cited by examiner

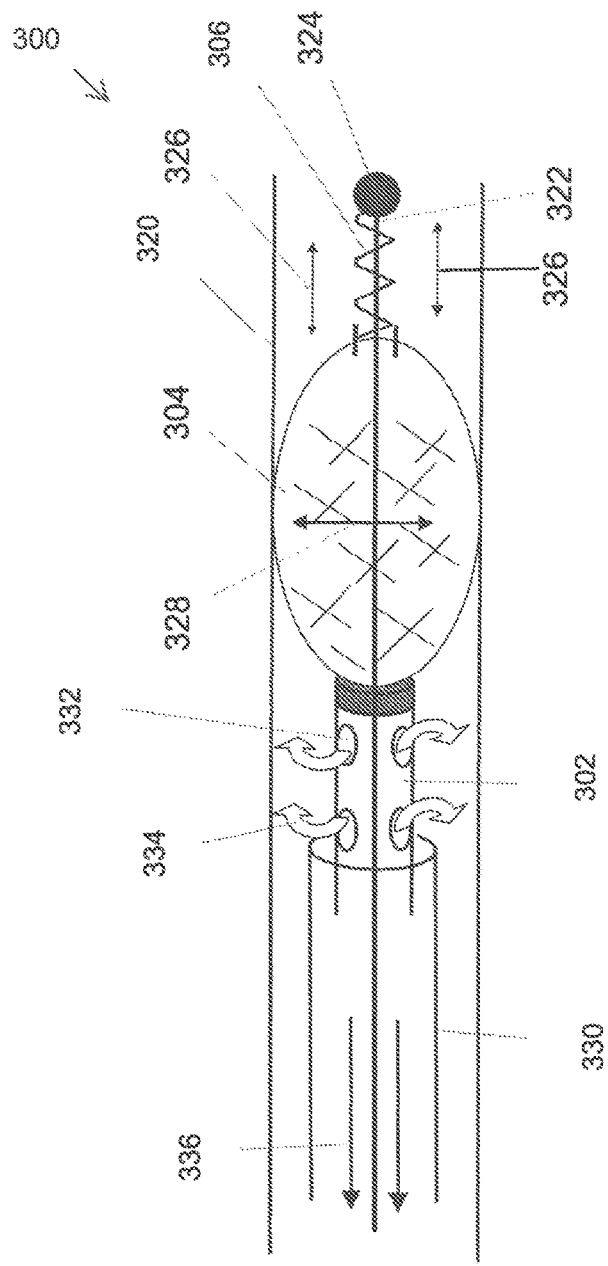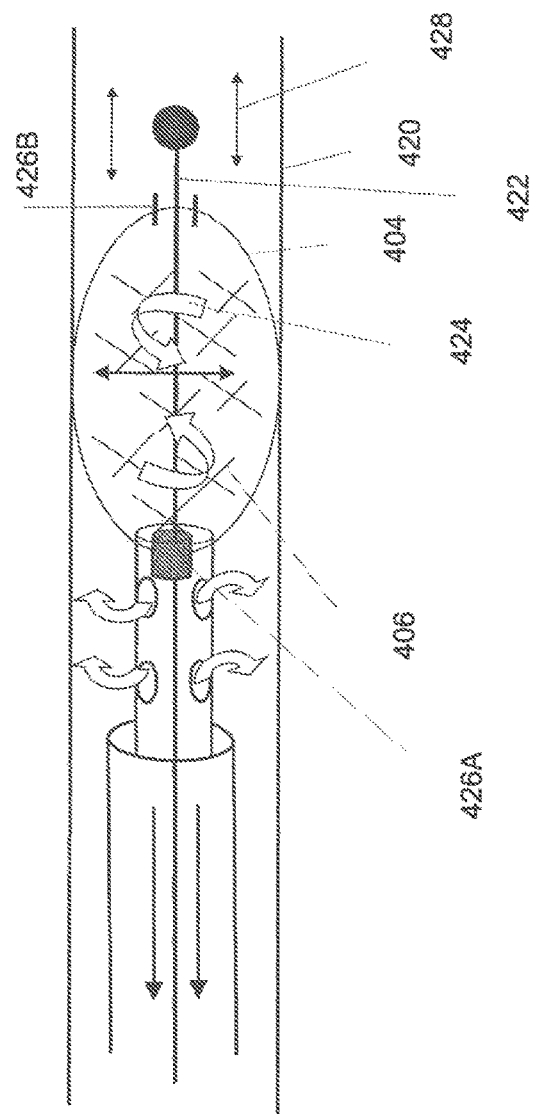
FIG. 3
FIG. 4

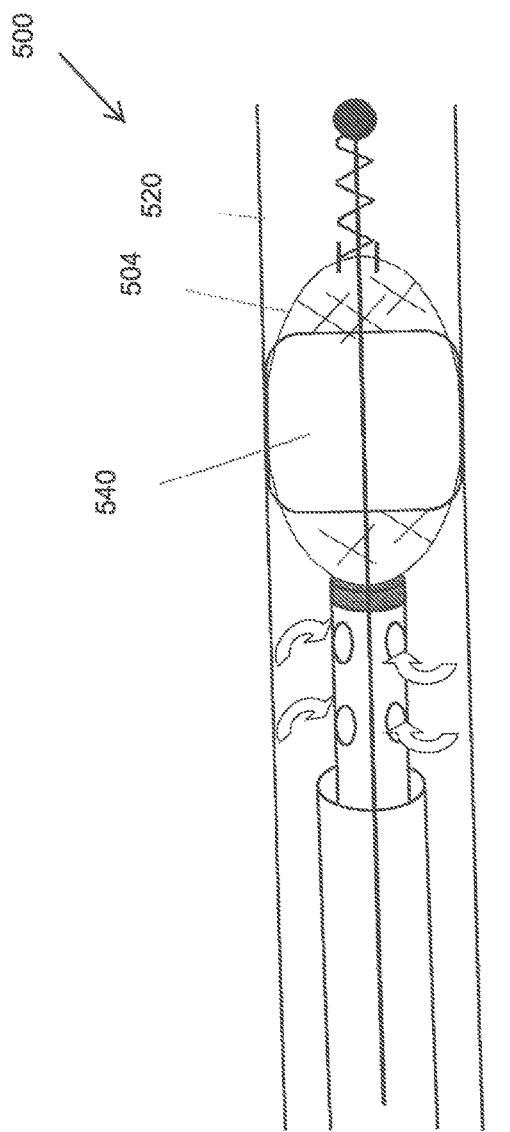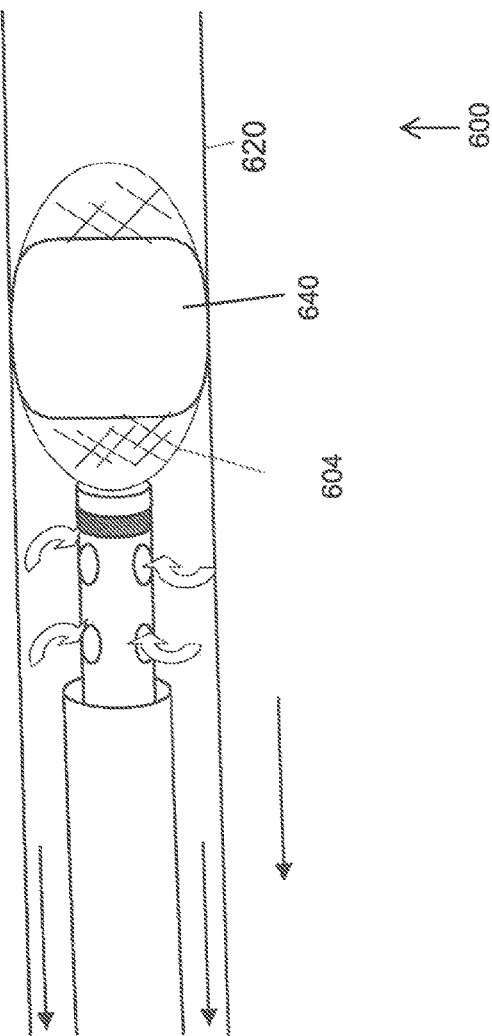
FIG. 5
FIG. 6

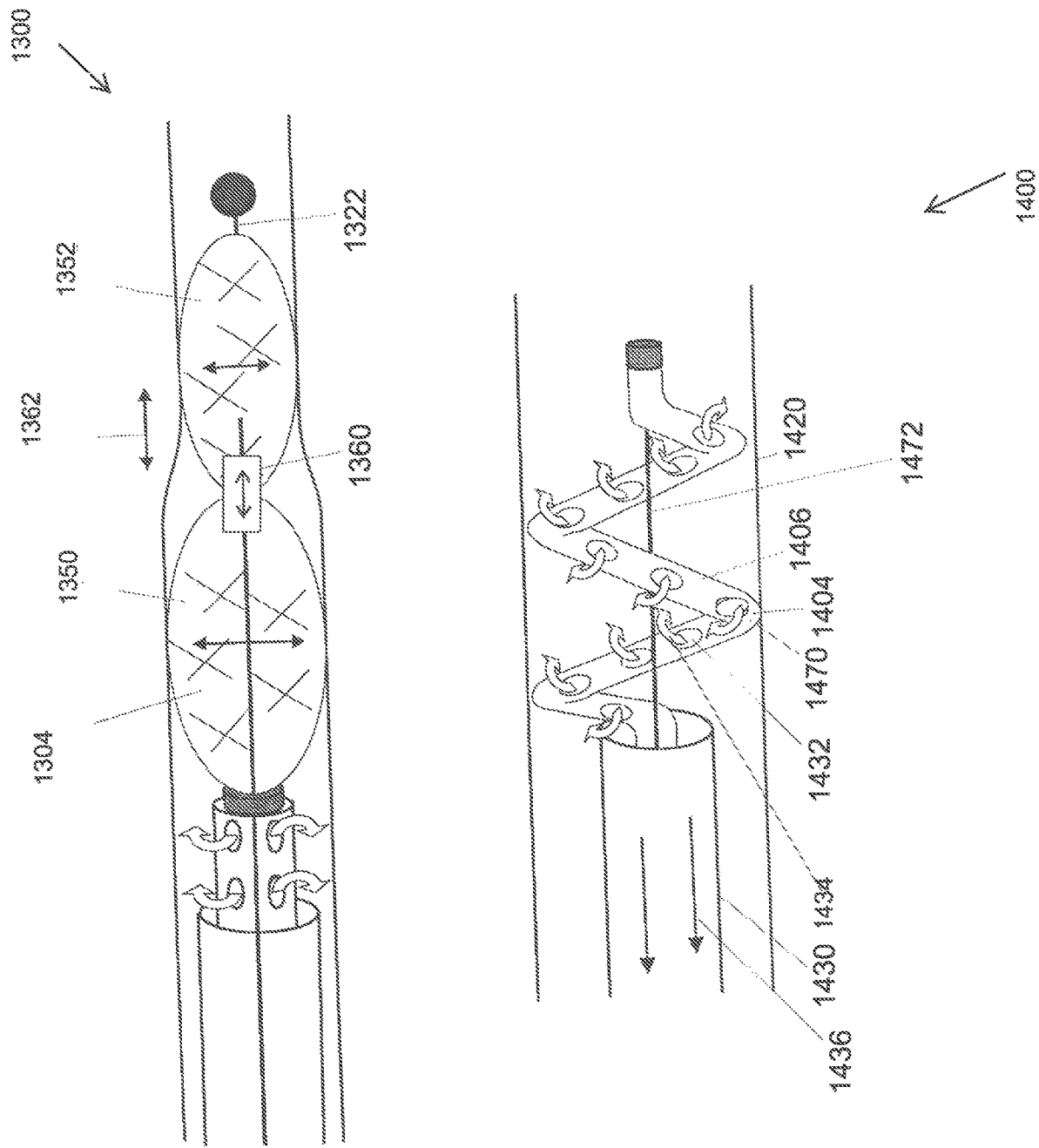

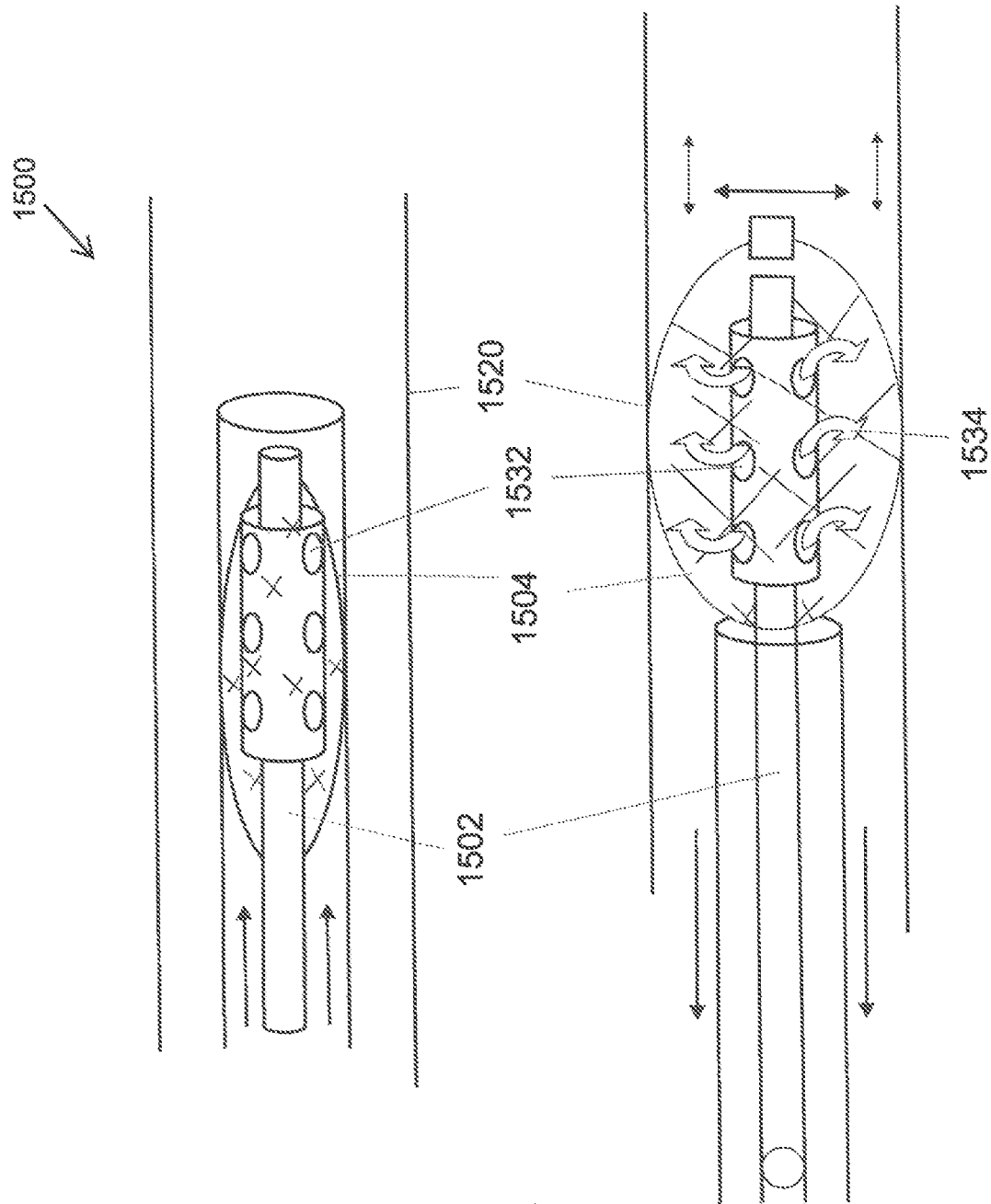

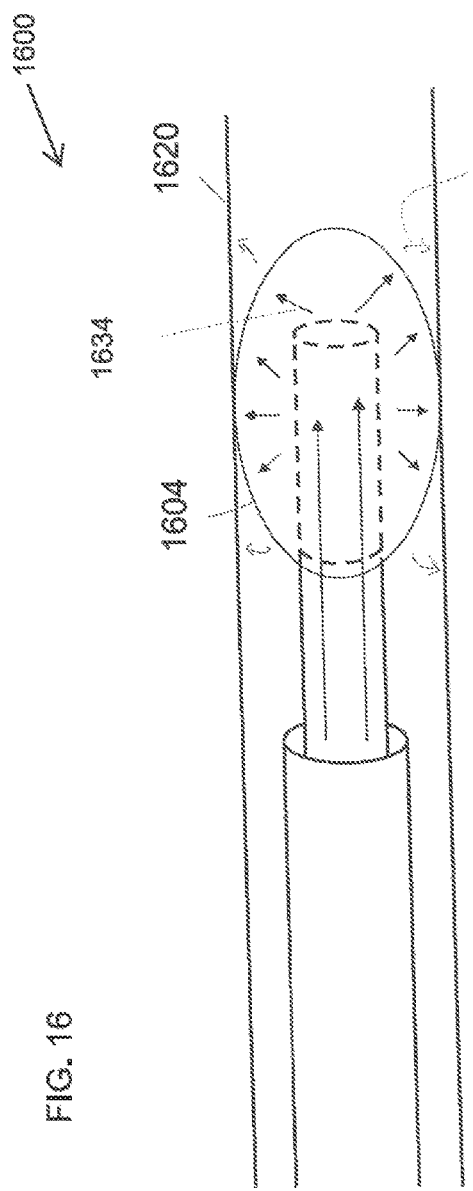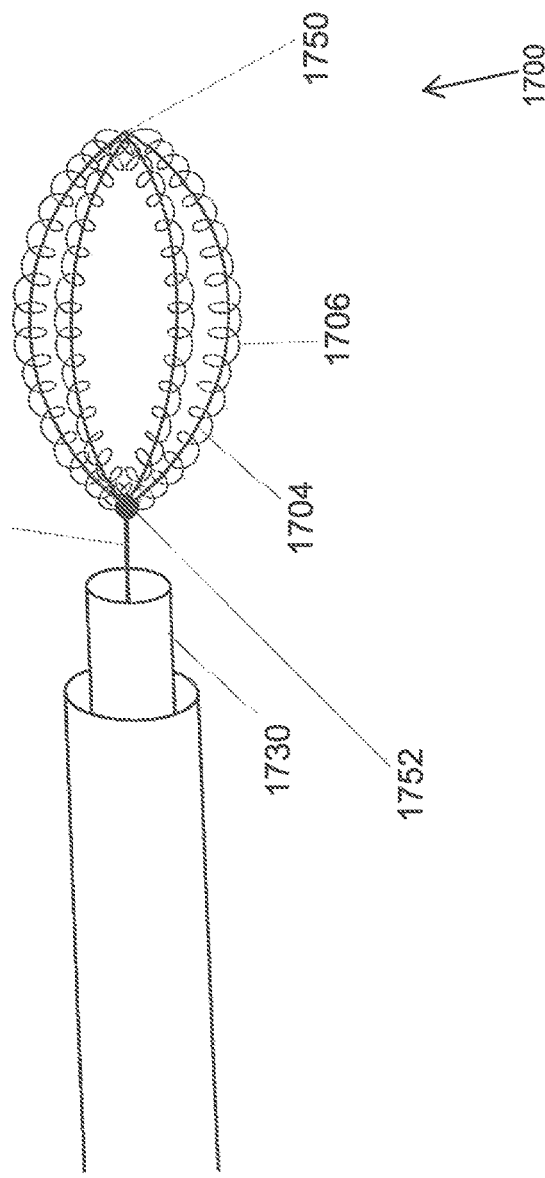
FIG. 16
FIG. 17

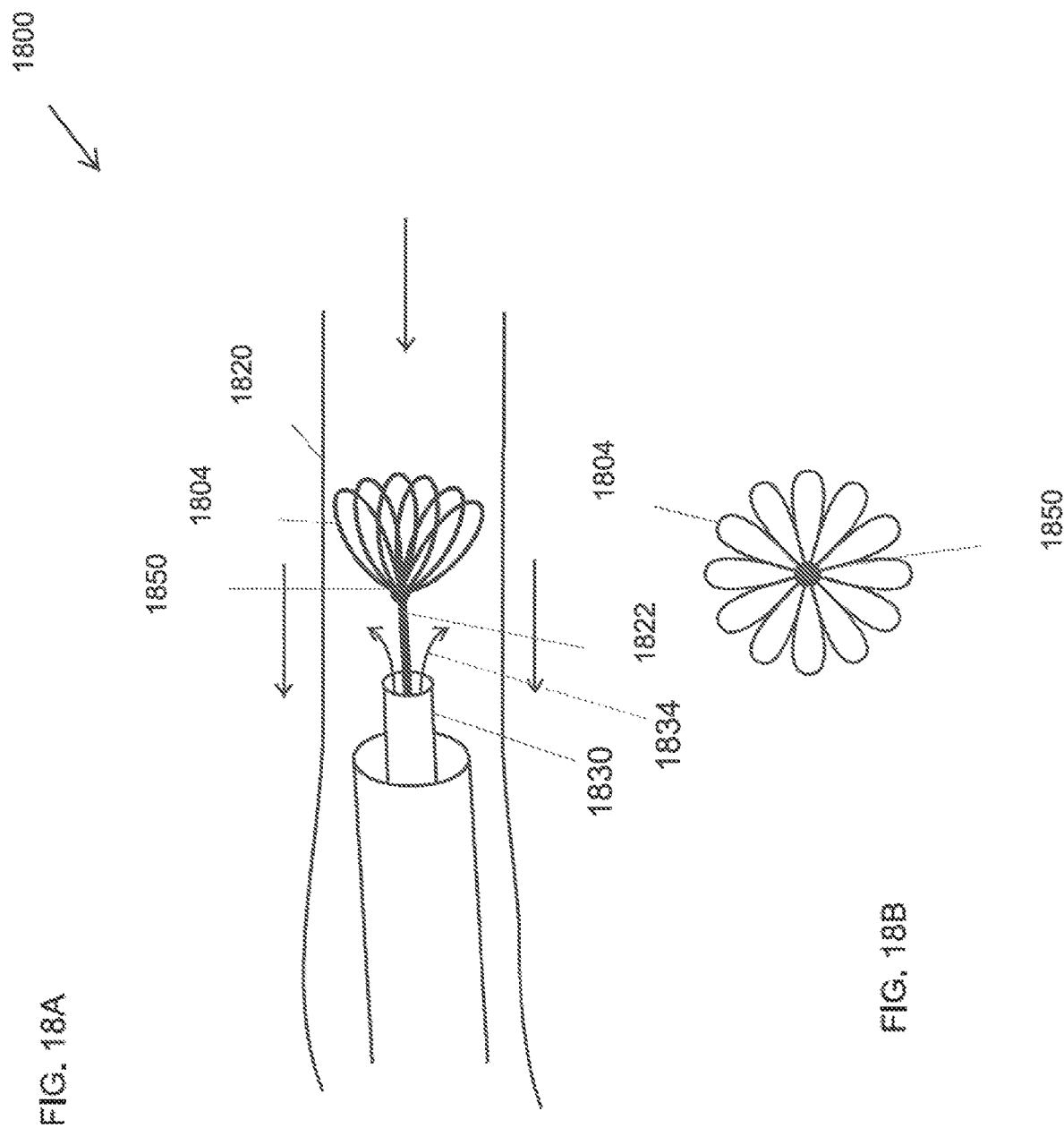

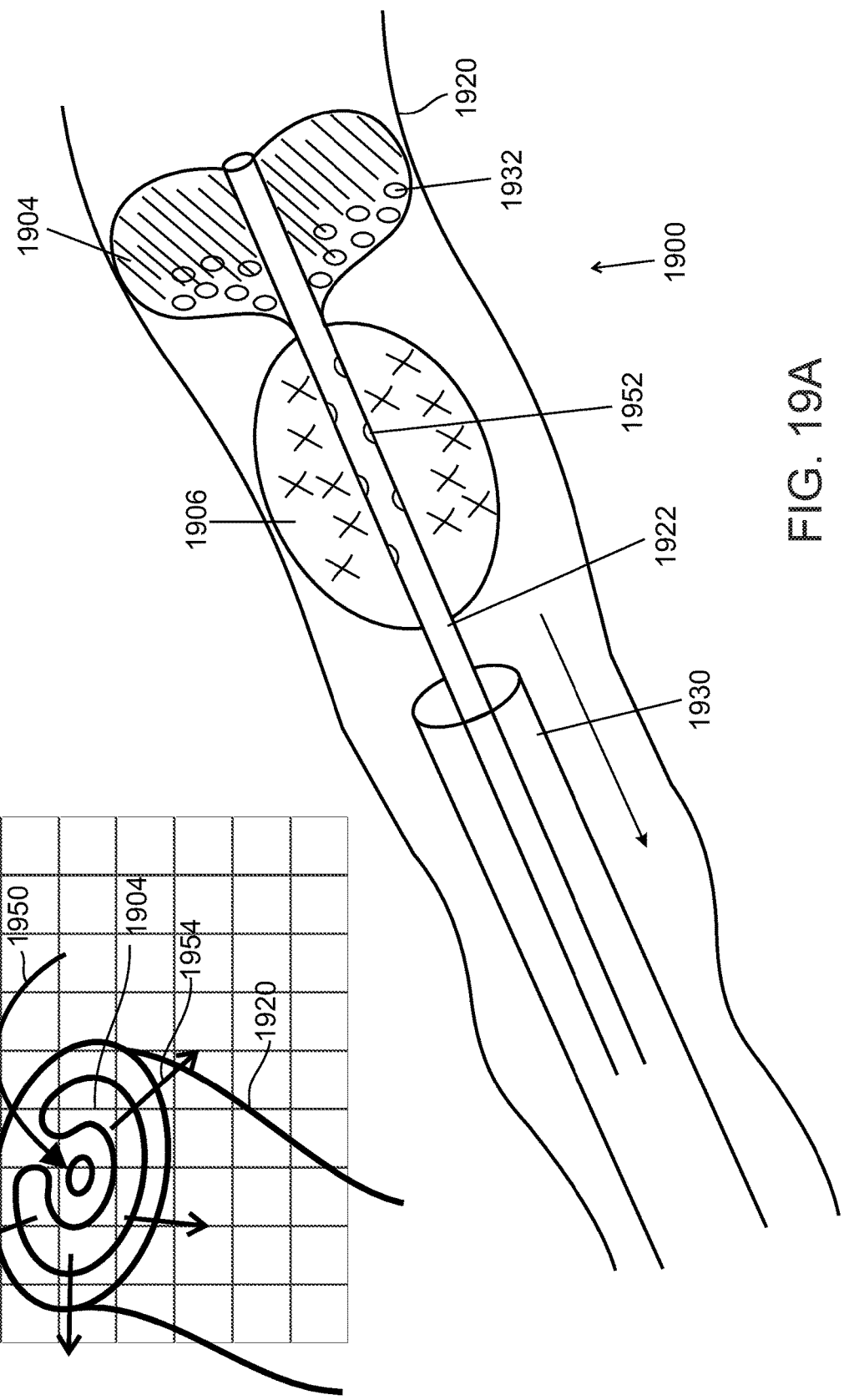

VEIN ABLATION DEVICE

RELATED APPLICATIONS

The present application is a National Phase of PCT Patent Application No. PCT/IL2014/050863 having International filing date of Oct. 1, 2014, which claims the benefit of priority under 35 USC § 119(e) of U.S. Provisional Patent Application No. 61/890,269 filed on Oct. 13, 2013. The contents of the above applications are all incorporated by reference as if fully set forth herein in their entirety. PCT Patent Application No. PCT/IL2014/050863 is related to co-filed, co-pending and co-assigned PCT Patent Application Nos. PCT/IL2014/050864 and PCT/IL2014/050862, both by the same inventor, Zeev Brandeis. PCT Patent Application No. PCT/IL2014/1050864 relates to devices and methods for synchronized injection and aspiration. PCT Patent Application No. PCT/IL2014/050862 relates to devices and methods for foam formation. The contents of the above applications are all incorporated by reference as if fully set forth herein in their entirety.

FIELD AND BACKGROUND OF THE PRESENT INVENTION

The present invention, in some embodiments thereof, relates to a device and/or method for vein ablation and, more particularly, but not exclusively, to a device and/or method for vein ablation by irritation.

Some patients suffering from vein disorders, for example varicose veins, are treated with the goal of closing off the vessel to blood flow. A variety of different methods and/or devices are available, such as non-invasive devices, surgical techniques, drug injections and/or minimally invasive devices. The non-invasive devices, such as compression stockings generally have limited efficacy, especially for more severe cases. The surgical techniques may produce better results, but with the risk of surgical complications. Cather based devices that emit energy (e.g., heat, radiofrequency, laser) run the risk of damage to nearby nerves and may not be very effective due to recanalization. Injection of liquid sclerosant directly in the vein is a fairly effective technique, but may be limited to short veins and/or veins with small diameters.

International Patent Application Publication No. WO 2009/109967 by Brandeis, the same inventor as the present application, discloses "A method for collapsing a target vein in a patient. The method comprises providing an intravascular irritation element having a plurality of mechanical irritating objects, inserting the intravascular irritation element into a venous lumen of a target vein, and irritating the target vein by moving the plurality of mechanical irritating objects in contact with the inner surface thereof, thereby triggering a collapse of said target vein."

In summary, Brandeis appears to teach mechanically irritating the vessel wall to trigger collapse of the vessel. A sclerosing agent may also be released to treat the vessel. Mechanical irritation, optionally together with chemical treatment, may be safer than other techniques, such as energy ablation and surgery, and may be more effective than, for example, sclerotherapy alone. The mechanical irritation with chemical injection may be used in vessels with larger diameters.

Additional background art includes International Patent Application Publication No. WO 2004/112569.

SUMMARY OF THE PRESENT INVENTION

An aspect of some embodiments of the present invention relates to a device for mechanically irritating the interior wall of a blood vessel for vein ablation, the device comprising an element to prop open the blood vessel against vessel spasm during the treatment.

According to an aspect of some embodiments of the present invention there is provided an endovascular catheter for vein ablation comprising: an elongated rod having a proximal end and a distal end portion, the elongated rod being sized for insertion into a vein; at least one irritation element coupled to the distal end portion of the elongated rod, the at least one irritation element having an expanded irritation state for contacting an inner wall segment of the vein to irritate the vein segment to trigger spasm of the vein segment and a non-irritation state, the at least one irritation element arranged for iterative changes between the irritation state and the non-irritation state; and at least one support element coupled to the distal end portion of the elongated rod, the support element arranged to apply a mechanical force from the distal end portion to iteratively return the irritation element to the expanded irritation state in response to dynamic feedback of vein walls pressing against the irritation element to force the irritation element into the non-irritation state.

According to some embodiments of the invention, the irritation element and the support element are combined into a flexible mesh woven from a first wire made of a rigidly arranged shape memory material and a second flexible wire arranged for contacting and irritating the inner wall of the vein segment.

According to some embodiments of the invention, the irritation element is a tubular mesh, and the support element is a resilient element biased to return the irritation element to the expanded irritation state.

According to some embodiments of the invention, the irritation element is a tubular mesh, and the support element is a balloon, the tubular mesh arranged around the outer surface of the balloon so that expansion of the balloon expands the tubular mesh.

According to some embodiments of the invention, the irritation element is a first tubular mesh, and the support element is a second tubular mesh having expandable and collapsible states, the first tubular mesh arranged around the second tubular mesh so that expansion of the second tubular mesh expands the first tubular mesh.

According to some embodiments of the invention, the catheter further comprises a fluid insertion channel having one or more first openings at the distal end portion, the first openings arranged for releasing a medical substance in near proximity to the vein segment.

According to some embodiments of the invention, the catheter further comprises a fluid removal channel having one or more second openings at the distal end portion, the second openings arranged for removing fluid and debris from the vein segment.

According to some embodiments of the invention, the catheter further comprises a controller arranged to simultaneously control the release of the medical substance and the removal of fluid and debris so that the medical substance is substantially retained within the vein segment.

According to some embodiments of the invention, one or both of the irritation element and the support element are coated with a sclerosing agent so that the sclerosing agent is delivered to the inner wall during the irritation.

According to some embodiments of the invention, the catheter further comprises a bearing that couples the irritation element to the distal end portion to provide self-rotational motion of the irritation element along a longitudinal axis of the catheter when the irritation element is dragged inside the vein. Optionally, the irritation element comprises a plurality of elevated parallel tracks arranged in a helical pattern on a surface thereof.

According to some embodiments of the invention, the support element comprises a first portion and a second portion arranged adjacently along the longitudinal axis of the catheter, so that compression of the first portion by the spasm is transferred to expansion of the second portion. Optionally, the first and second portions are part of a single tubular mesh structure having a constricted region separating the first and second portions.

According to some embodiments of the invention, the support element is a balloon comprising a plurality of pores arranged to release a sclerosing agent in proximity to the inner wall.

According to some embodiments of the invention, one or both of the irritation element and the support element are impregnated with a sclerosing agent so that the sclerosing agent is delivered to the inner wall during contact with the inner wall.

According to some embodiments of the invention, the irritation element is made from a resilient material with an elasticity coefficient adapted to scratch the inner wall without irritating tissue surrounding the inner wall.

According to some embodiments of the invention, the irritation element is expanded to a diameter larger than the rest diameter of the vein so that the inner wall of the vein is damaged by the expansion.

According to an aspect of some embodiments of the present invention there is provided a method of vein ablation comprising: propping open a vein segment from a collapsed state; mechanically irritating an inner wall of the vein segment so that the inner wall collapses or spasms; applying a mechanical force from inside the vein segment to iteratively return the vein segment to the propped open state against the spasm or collapse, the mechanical force applied in response to dynamic feedback of the vessel wall that forces the vein segment back to the collapsed state; and irritating the vein segment during the iterative returns to the propped open state. Optionally, the method further comprises delivering a sclerosing agent to the inner wall during one or more of the propping open, mechanically irritating, applying, and irritating.

According to some embodiments of the invention, the method further comprises removing blood and some of the delivered sclerosing agent from the vein segment, the delivery and the removing controlled so that the sclerosing agent is substantially retained within the vein segment.

According to some embodiments of the invention, the method further comprises removing the propping open of the vein segment, allowing the vein segment to collapse, and treating another adjacent vein segment.

According to some embodiments of the invention, mechanically irritating comprises contacting the inner wall in a plurality of locations simultaneously to form helical patterns along a longitudinal axis of the vein.

According to some embodiments of the invention, the method further comprises transferring constrictive spasm forces from a first vein segment to prop open a second vein segment.

According to an aspect of some embodiments of the present invention there is provided an endovascular catheter for vein ablation comprising: an elongated rod having a proximal and a distal end portion, the elongated rod being sized for insertion into a vein; at least one irritation element coupled to the distal end portion of the elongated rod and arranged for contacting an inner wall of the vein segment to irritate and trigger spasm of the vein segment; and a bearing arranged to couple the irritation element to the distal end portion so that the irritation element is independently rotatable along a longitudinal axis of the rod, so that the irritation element irritates the inner wall in a helical pattern as the irritation element self-rotates by displacement along a longitudinal axis of the vein.

According to some embodiments of the invention, the irritation element comprises one or more rails arranged in a spiral pattern on a surface.

According to some embodiments of the invention, the catheter further comprises at least one support element coupled to the distal end portion of the elongated rod, the support element being rigid to prop open the vein segment and return the vein segment to the propped open state against the spasm. Optionally, the support element is coupled to one or both of the coupling mechanism and the irritation element so that the support element is able to rotate along the longitudinal axis of the rod.

According to an aspect of some embodiments of the present invention there is provided an endovascular catheter for vein ablation comprising: a first elongated rod having a proximal end and a distal end portion, the elongated rod being sized for insertion into a vein, the distal end portion having an expanded helical shaped state with at least one bend for contacting and irritating an inner wall of a segment of the vein, and a non-irritating state; a second rigid rod mechanically coupled to the distal end of the first rod so that proximal or distal displacement of the second rod iteratively changes the first rod between the irritating state and the non-irritating state.

According to some embodiments of the invention, the catheter further comprises a support element coupled to the first and second rods, the support element arranged to automatically apply a mechanical force from the distal end portion of the first rod to iteratively return the helix to the expanded irritation state in response to dynamic feedback of the vein segment walls pressing against the helix to force the helix to the non-irritation state.

According to some embodiments of the invention, the helix is a hollow tube having at least one opening for releasing a sclerosant in proximity to the inner vein wall, the at least one opening located away from the at least one bend of the helix.

Unless otherwise defined, all technical and/or scientific terms used herein have the same meaning as commonly understood by one of ordinary skill in the art to which the present invention pertains. Although methods and materials similar or equivalent to those described herein can be used in the practice or testing of embodiments of the present invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings:

FIG. 3 is a schematic illustration of a vein treatment catheter, in accordance with embodiments of the present invention;

FIG. 4 is a schematic of another vein treatment catheter, in accordance with embodiments of the present invention;

FIG. 5 is a schematic of yet another vein treatment catheter, in accordance with embodiments of the present invention;

FIG. 6 is a schematic of yet another vein treatment catheter, in accordance with embodiments of the present invention;

FIG. 13 is a schematic of yet another vein treatment catheter, in accordance with embodiments of the present invention;

FIG. 14 is a schematic of yet another vein treatment catheter, in accordance with embodiments of the present invention;

FIGS. 15A-B are schematics of yet another vein treatment catheter, in accordance with embodiments of the present invention;

FIG. 16 is a schematic of yet another vein treatment catheter, in accordance with embodiments of the present invention;

FIG. 17 is a schematic of yet another vein treatment catheter, in accordance with embodiments of the present invention;

FIGS. 18A-B are schematics of yet another vein treatment catheter, in accordance with embodiments of the present invention; and FIGS. 19A-B are schematics of yet another vein treatment catheter, in accordance with embodiments of the present invention.

DESCRIPTION OF SPECIFIC EMBODIMENTS OF THE PRESENT INVENTION

Figure 1:
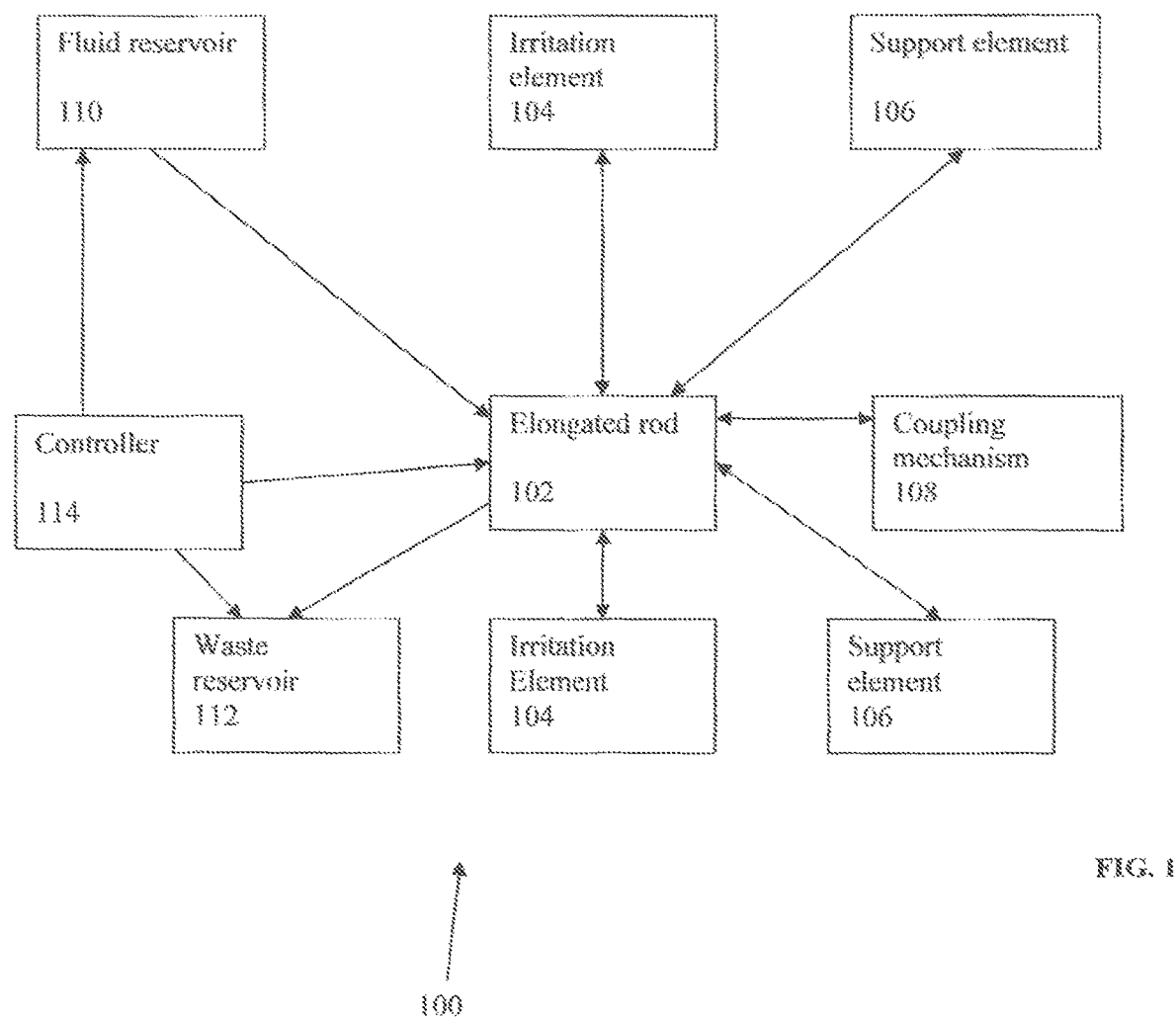
FIG. 1 is a block diagram of a catheter for treating veins, in accordance with exemplary embodiments of the present invention.

As used herein, the term "proximal" means closer to the operator of the catheter.

As used herein, the term "distal" means further away from the operator of the catheter.

As used herein, the phrase "inner wall" means the inner tissue layer of the vein wall, the intima or endothelial cell layer.

An aspect of some embodiments of the present invention relates to endovascular catheters and/or methods of use thereof where a catheter comprises an irritation element at a distal end thereof to irritate an inner wall of a vein segment, and a support element at a distal end portion thereof to apply a mechanical force from the distal end portion to iteratively return the irritation element to the expanded irritation state in response to dynamic feedback of vein walls pressing against the irritation element to force the irritation element into the non-irritation state. Optionally, the force applied by the support element returns the irritation element to the irritation state during a spasm of the vein segment. Alternatively or additionally, the support element returns the irritation element to the irritation state during a mechanical ablation, for example, scratching of the inner vein wall. Alternatively or additionally, the support element returns the irritation element to the irritation state during treatment with a sclerosant agent.

Advantageously, the support element provides additional mechanical force over any inherent expansion forces of the irritation element alone to return the irritation element to the irritation state. Advantageously, using the support element may allow the irritation element to be designed to achieve a desired irritation without having to trade the desired irritation for expansion force.

Advantageously, the support element returning the irritation element to the irritation state may allows drugs and/or additional mechanical damage to be delivered to the inner wall as compared to the non-irritation state in which the vein segment collapses and/or narrows during the spasm.

Optionally, the irritation element disposed at the distal end portion of a catheter irritates the inner wall simultaneously at a plurality of regions. Optionally, the irritation is performed circumferentially around the inner wall of the propped open vein segment.

Optionally, the support element (or two connected support elements) converts compressive forces from the vein spasm at a first portion of the distal end portion, into expansion forces to prop open a vein at a second portion of the distal end portion.

Optionally, the support element is arranged to return the irritation element to the irritation state so that the irritation element contacts the inner vessel wall in a desired pattern. Optionally, the irritation element in the non-irritation state does not fully contact the inner wall to achieve the desired irritation. The irritation element may be partially or fully contracted, and/or the irritation element may not contact the inner wall in the desired pattern.

Optionally, the support element is arranged to return the irritation element to the irritation state so that the irritation element props open the inner vessel wall.

Optionally, there are two ablation types, a first mechanical ablation and a second chemical ablation. Optionally, the vein is propped open during the first ablation.

Optionally, the first ablation triggers a spasm. Optionally, the vein segment is returned to the propped open state during the spasm by the support element returning the irritation element to the irritation state, so as to allow the second ablation. Advantageously, returning to the irritation state of the irritation element and propping open the vein with the mechanically damaged (e.g., scratched) inner wall may allow better delivery of the sclerosant agent to the damaged inner wall, as compared to allowing the vein to spasm without propping open. In this manner, the vein collapse may be controlled until the wall has been fully treated. The vein segment may be allowed to collapse after the treatment of the wall of the vein segment has been completed.

Optionally, the irritation element irritates and/or damages the inner wall so that the vein segment spasms. Optionally, scratches (e.g., by small needles) damage the inner wall. Alternatively or additionally, chemicals (e.g., sclerosant drugs) damage the inner wall. Alternatively or additionally, overextension (e.g., balloon overexpansion) damages the inner wall.

Optionally, a sclerosant agent is delivered in proximity of the propped inner wall.

Optionally, the sclerosant agent is delivered to the propped inner wall during the spasm. Optionally, the sclerosant agent is delivered directly to the propped damaged wall by contact of the catheter with the vessel wall.

Optionally, the delivery of the sclerosant agent is coordinated with the removal of the sclerosant agent in the blood stream. Optionally, the delivery and removal are synchronized so that the sclerosant agent is retained within the treatment vein segment, without clinically damaging amounts of sclerosant being released into other vessels.

Optionally, the catheter comprises an expandable irritation element at a distal end portion thereof to over-stretch an inner wall of a vein segment past the rest diameter of the inner wall, so that the inner wall is damaged. Optionally, the over-stretch causes the vein segment to spasm. Vein walls are thinner, less muscular and/or weaker as compared to artery walls, so that much less force and/or pressure may be required to cause damage.

Optionally, the over-stretch of the vein is performed without damaging tissue outside the vein and/or without damaging the deeper layers of the vein wall so that blood does not leak out of the vein. In some cases, some damage to the vessel wall is allowed, for example, some bruising may result from the treatment.

An aspect of some embodiments of the present invention relates to an endovascular catheter and/or method of use thereof, the catheter comprising an irritation element coupled to the distal end portion of the catheter with a bearing, the bearing arranged so that the irritation element is able to self-rotate independently of the rest of the catheter. The rotation is driven by forces applied by the vein itself, as the catheter is displaced within the vein. Optionally, the rotation is in a helical pattern relative to the vein wall. Advantageously, only the distal end portion of the catheter may be rotated, without requiring a longitudinal rod or other stiff element to deliver torque from outside the body. Advantageously, rotation is provided without the need for a motor, without an external rotating force and/or without applying an actuating force.

Optionally, the bearing is arranged to rotate the irritation element along the longitudinal axis of the catheter. When inside the vein, the longitudinal axis of the catheter is substantially coaxial with the longitudinal axis of the vein.

Optionally, the irritation element is arranged so that displacement along the longitudinal axis of the vein self-rotates the irritation element along the longitudinal axis of the catheter. Optionally, the self-rotating irritation element scratches the vein wall in a helical pattern around the circumference of the wall. Optionally, the scratching is performed at multiple points to scratch in multiple helical abrasion patterns. Optionally, scratching may only be performed in the helical pattern, as rotation of the irritation element only occurs during displacement along the longitudinal axis. Advantageously, the scratching is controlled by the displacement, possibly allowing finer control over the irritation to the inner wall. For example, as rotation only occurs during displacement, the physician may let go of the catheter without risk of unwanted irritation and pull the catheter when irritation is desired.

An aspect of some embodiment of the present invention relates to an endovascular catheter for vein ablation comprising an elongated rod having at a distal end thereof a helical shape. The helix has an expanded irritating state with at least one bend for contacting and irritating an inner wall of a segment of the vein, and a non-irritating state. A rigid rod mechanically coupled to the helix iteratively transitions the helix between the irritating state and the non-irritating state.

The present invention, in some embodiments thereof, relates to a device and/or method for vein ablation and, more particularly, but not exclusively, to a device and/or method for vein ablation by irritation.

Before explaining at least one embodiment of the present invention in detail, it is to be understood that the present invention is not necessarily limited in its application to the details of construction and the arrangement of the components and/or methods set forth in the following description and/or illustrated in the drawings and/or the Examples. The present invention is capable of other embodiments or of being practiced or carried out in various ways.

Referring now to the drawings, FIG. 1 is a block diagram of components of an exemplary vein treatment catheter 100, in accordance with embodiments of the present invention. Optionally, catheter 100 comprises one or more support elements 106 arranged to apply a mechanical force from the distal end portion of catheter 100 to iteratively return an irritation element 104 to the expanded irritation state in response to dynamic feedback of vein walls pressing against irritation element 104 to force irritation element 104 into the non-irritation state. Optionally, alternatively or additionally, catheter 100 comprises a coupling mechanism 108 arranged so that irritation element 104 is able to self-rotate independently of the rest of catheter 104.

In exemplary embodiments, one or more irritation elements 104 disposed at the distal end portion of catheter 100 mechanically irritate the inner wall of the vein segment in an amount sufficient to trigger spasm of the vein segment. Catheter 100 may achieve clinically selected vein closure, obliteration, scarring, sclerosis and/or obstruction so that blood flow through the vein is prevented or reduced in a clinically selected manner thereby treating the patient. Optionally, the vein treatment is permanent.

Optionally, catheter 100 is delivered into the vein through an outer sheath.

Optionally, the sheath maintains one or more components of catheter 100 in a compressed state.

Optionally, irritation element 104 scratches the inner wall. Optionally, irritation element 104 is, for example, a woven mesh. Optionally, irritation element 104 comprises multiple smaller scratching elements adapted to scratch the wall, for example, small pins, sharp edges, small round spheres, or other suitable shapes, or alternatively, no additional scratching elements are used. Alternatively or additionally, irritation element 104 damages the wall by over-stretching the vein, for example, a balloon or tubular mesh are expanded in the vein to a diameter larger than the rest diameter of the vein, and/or beyond the elastic limit of the vein. Alternatively or additionally, irritation element 104 chemically irritates the inner wall.

Optionally, irritation element 104 is collapsible for insertion into the vein.

Optionally, irritation element 104 is expandable inside the vein so that irritation element 104 contacts the inner wall of the vein.

Optionally, irritation element 104 is made from a resilient material with an elasticity coefficient adapted to scratch the inner wall without irritating tissue surrounding the inner wall.

Some examples of possible irritation elements 104 in accordance with embodiments of the present invention may be found, for example, in International Patent Application Publication No. WO 2009/109967 by the same inventor of the present application, hereby incorporated by reference in its entirety. For example, element 104 is any suitable mechanical irritating objects, such as bristles, pins, wires, studs, anchors, knives, filers, hooks, and/or any type of scratchers.

Catheter 100 comprises an elongated rod 102, having distal and proximal end portions. Optionally, rod 102 is rigid so as to allow transmission of a torque and/or displacement force from outside the body to a distal end thereof by the entire rod 102 rotating and/or displacing when the proximal end portion is rotated and/or displaced.

Optionally, rod 102 is a hollow tube.

The catheter 100 is available in a variety of sizes suitable for insertion into a variety of vein diameters requiring treatment, for example, about 0.67 mm, about 1 mm, about 1.33 mm, about 1.67 mm, about 2 mm, about 3 mm, about 5 mm, or other smaller, intermediate or larger sizes. Optionally, irritation element is located at the distal end portion of rod 102.

Optionally, one or more support elements 106 are coupled to the distal end portion of rod 102. Support element 106 is made out of a rigid material and/or has a rigid design to open the vein (vein walls may be collapsed during catheter insertion).

Optionally, support element 106 is arranged to open the vein segment into the resting cross sectional shape. Alternatively, the vein segment walls are stretched beyond the rest diameter to damage the inner wall. The cross sectional shape may be limited by the properties of the vein wall at the opened segment, for example, substantially circular, substantially ellipse, or other regular or irregular shapes.

Optionally, support element 106 applies a mechanical force so as to return the vein to the open state against forces applied by the collapsing vein walls. Alternatively or additionally, support element 106 applies a mechanical force to return the vein to the open state against spasm of the vein. The spasm may be triggered by irritation element 104.

Optionally, a balance is achieved in the rigidity, resiliency and/or flexibility of support element 106 so that element 106 opens and/or returns the vein segment to the open state while allowing displacement of element 106 along the longitudinal axis of the vein while element 106 applies the mechanical force to return the vein segment to the open state, the displacement being performed without significant damage to the vein and/or surrounding tissues (e.g., rupture of the vein wall, damage to nerves, damage to adjacent blood vessels, deep scratches of the vein wall that allow blood to leak out).

Optionally, irritation element 104 and support element 106 are two separate elements. Some examples of arrangements include: disposed side by side along the longitudinal axis of rod 102, encircling one another, and/or intertwined. Optionally, support element 106 is arranged to not irritate the inner vessel wall, for example, by being located and/or arranged so that element 106 does not contact the inner wall, and/or by having a smooth surface. Alternatively, support element 106 is arranged to irritate the inner vessel wall, for example, by having scratching elements disposed on the surface contacting the inner wall. Alternatively or additionally, irritation element 104 and support element 106 are combined into a single element.

Optionally, a coupling mechanism 108 couples irritation element 104 and/or support element 106 to the distal end portion of rod 102. Optionally, coupling mechanism 108 is a bearing. Optionally, coupling mechanism 108 allows elements 104 and/or 106 to rotate. Optionally, elements 104 and/or 106 rotate at the distal end portion without catheter components proximal to the bearing rotating. Optionally, elements 104 and/or 106 rotate at the distal end portion of rod 102 without requiring torque delivery from an external source, for example, without requiring a wire to turn, the wire being turned by a power source external to the body.

Optionally, a fluid reservoir 110 is in fluid communication with rod 102.

Optionally, rod 102 comprises one or more fluid insertion channels to provide fluid communication between fluid reservoir 110 and the distal end portion of rod 102.

Some examples of possible fluids that may be injected into the vein to treat the vein include; a liquid sclerosant, a foam sclerosant. Some examples of sclerosant agents include; sodium tetradecylsulphate (e.g., about 0.1-3%), and/or polidocanol (e.g., about 0.5-3%).

Optionally, rod 102 comprises one or more injection openings at the distal end portion thereof, the openings arranged to allow fluid from reservoir 110 to flow in proximity to the inner wall of the vein segment.

Optionally, reservoir 110 is located outside the body. Alternatively or additionally, reservoir 110 is located on the distal end of rod 102, for example, integrated with irritation element 104.

Optionally, a waste reservoir 112 is in fluid communication with rod 102.

Optionally, rod 102 comprises one or more waste removal channels to provide fluid communication between waste reservoir 112 and the distal end portion of rod 102.

Optionally, rod 102 comprises one or more removal openings at the distal end portion thereof, the openings arranged to allow waste (e.g., blood, injected fluid, clots) from the treated vein segment to flow out of the body to waste reservoir 112.

Optionally, a controller 114 (e.g., mechanical mechanism, customized circuitry, programmed computer) controls the fluid insertion from reservoir 110 and the removal of substances from the vein to reservoir 112. Optionally, the control is performed so that injected fluid is retained in the treated vein segment without clinically damaging amounts of injected fluid flowing out of the vein segments to other parts of the body.

Alternatively or additionally, controller 114 controls the displacement of rod 102 inside the vein. Control of controller 114 may be manual (e.g., by the surgeon) and/or automatic (e.g., by software).

Additional details of a possible suitable device to control the fluid injection and/or removal may be found, for example, in International Patent Application Publication No. WO2009/104189 by the same inventor of the present application, hereby incorporated by reference in its entirety.

Figure 2:
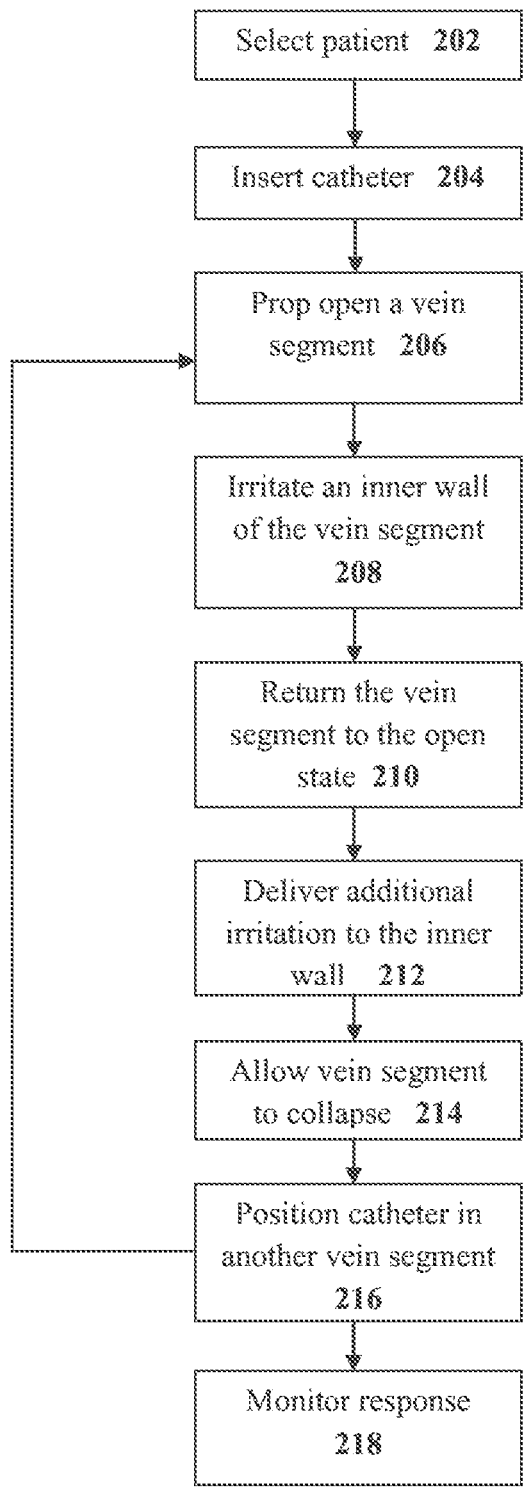
FIG. 2 is a method of treating veins, for example, using the catheter as depicted in FIG. 1, in accordance with exemplary embodiments of the present invention.

Reference is now also made to FIG. 2, which is a flowchart of a method of operation of the vein treatment catheter and/or a method of treating veins using the vein treatment catheter, in accordance with embodiments of the present invention. Vein treatment catheters suitable for performing the method include, for example, catheter 100 of FIG. 1, or other catheters as described herein. Optionally, the method returns the vein segment to the open state to allow the inner wall to be mechanically and/or chemically damaged so that the vein segment is ablated in a clinically selected manner. Advantageously, the method may keep the vein segment in the open state for a longer cumulative period of time, and therefore the vein may experience more damage, as compared to, for example, methods that do not return the vein to the open state.

Optionally, at 202, the patient is selected for treatment by the vein treatment device and/or method as describe herein, in accordance with embodiments of the present invention. Optionally, the patient is selected for treatment of a blood vessel disorder, for example, a spider vein, a varicose vein, hemorrhoids, and/or varicocele. Optionally, the patient is selected for treatment by a caretaker, for example, by the physician according to guidelines.

Optionally, the treatment plan for the patient is selected. Optionally, the surgeon decides on one or more target vein segments to treat, for example, segments of the: perforator veins, tributaries, the great saphenous vein, the small saphenous vein, or other vessels.

Optionally, at 204, the vein is accessed (e.g., micropuncture) and the catheter is inserted into the vein, in accordance with embodiments of the present invention.

Optionally, a hollow sheath is inserted first for access. Alternatively or additionally, the vein treatment device is inserted together with the hollow sheath, or following the hollow sheath insertion.

Optionally, the vein is accessed at the vein segment to be treated last, for example, at the thigh if varicose veins are treated. Optionally, the catheter is threaded in the direction opposite to the blood flow to reach the first segment to be treated (e.g., closer to the ankle).

At 206, the vein segment is propped open, in accordance with embodiments of the present invention. The vein segment may be found in the collapsed state during insertion of the catheter. The collapsed state may be the natural state of the vein segment, even before any treatment has been performed.

Optionally, the vein segment is propped open by the support element contacting the inner wall of the vein segment. Optionally, the support element is expanded from the contracted state to the expanded state, the change in state opening up the vein segment.

Alternatively or additionally, the support element is already in the expanded state, but is displaced (along the longitudinal axis of the vein) from a first open vein segment to a second closed vein segment. The second vein segment being opened as the support element is being displaced into the second vein segment.

At 208, the inner wall of the vein is irritated, in accordance with exemplary embodiments of the present invention. Optionally, the inner wall is irritated by the irritation element. Optionally, the irritation element is expanded from a contracted state to an expanded irritation state to contact the inner wall. Optionally, the vein segment is irritated by the contact with the irritation element.

Optionally, the irritation is mechanical, for example, an abrasion, a scratch, a peel, or a catch. Alternatively or additionally, the irritation is chemical, for example, a sclerosant agent.

Optionally, the vein segment is irritated so that the vein segment spasms.

At 210, the vein segment is returned to the open state against the vein segment spasm, in accordance with exemplary embodiments of the present invention. Optionally, the support element applied mechanical forces to return the vein segment to the open state.

Some reduction in the cross sectional diameter of the open state of the vein segment under the spasm forces and/or tendency to collapse may be allowed while still maintaining the open state and/or the irritation state of the irritation element, for example, no more than about 10%, or about 20%, or about 30%, or about 50%.

Optionally, at 212, the vein segment is irritated during the spasm, in accordance with exemplary embodiments of the present invention.

Optionally, the irritation during the spasm is in addition to the irritation before the spasm, as in box 208.

Optionally, the irritation during the spasm is mechanical. Alternatively or additionally, the irritation during the spasm is chemical.

Optionally, during the chemical irritation of 212 and/or 208, some of the drug in the vein, blood, clots and/other substances in the vein are removed. Optionally, the removing is controlled together with injection of the drug so that the drug is mostly retained within the vein segment.

At 214, the vein segment is allowed to collapse. Optionally, the vein is collapsed by the spasm triggered by the irritation. Alternatively or additionally, the vein segment is collapsed by the removal of the support element.

Optionally, the support element is contracted, allowing the vein segment to collapse. Alternatively, the support element is removed from the vein segment by distal displacement.

Optionally, at 216, the treatment catheter is positioned in another vein segment.

Optionally, the catheter is proximally displaced along the longitudinal axis of the vein. Optionally, the displacement occurs in the direction of blood flow, so that the catheter may more easily pass through valves in the vein.

Optionally, the treatment of the vein segments proceeds as in 206.

Optionally, the treatment of vein segments is continuous, the catheter being continuously proximally displaced. Alternatively or additionally, the treatment is performed in a discrete and/or step wise manner, with nearby, adjacent, overlapping and/or spaced apart vein segments being individually treated.

Optionally, at least some of the displacement and/or treatment is automatically controlled by the controller. Alternatively or additionally, at least some control is manually provided by the caregiver.

Optionally, the irritation occurs together with the displacement. Optionally, the irritation is performed as several helixes along the inner wall, the helical pattern arranged along the longitudinal axis of the vein.

Optionally at 218, the response to the treatment by the patient is monitored. Optionally, monitoring is performed within a short period of time after and/or during the procedure. For example, the patient is clinically observed and/or examined for venous spasm. In another example, the vein is imaged using ultrasonography for the presence of a thin white line on the venous wall. Alternatively or additionally, long term monitoring is performed. For example, the patient is examined weeks or months after the treatment to look for recurrence.

Reference is now also made to FIG. 3, which is a schematic illustration of a vein treatment catheter 300, in accordance with embodiments of the present invention. Catheter 300 comprises a resilient support element (e.g., a spring 306) arranged to apply a force to an irritation element from the distal end portion of catheter 300, for example a tubular mesh 304, so that mesh 304 is returned to an expanded irritation state.

Optionally, supported mesh 304 props open a wall of a vein segment 320.

Optionally, mesh 304 is returned to the expanded irritation state against forces applied by collapsing vein walls, such as during a spasm. Optionally, supported mesh 304 is in contact with the inner wall of vein 320, optionally around the circumference. Advantageously, the inner wall of vein 320 may be scratched around the inner circumference, even as the walls tend to collapse or spasm inwards.

Optionally, mesh 304 is coupled (affixed or pushed against) at a first end thereof to a hollow rod 302. For example, mesh 304 is tapered at the first end, and secured at the first end.

Optionally, mesh 304 is at least partly made out of a shape memory material, for example, Nitinol. Optionally, upon insertion into the vein segment, mesh 304 self expands to contact the inner vein wall. Alternatively or additionally, mesh 304 is at least partly made out of a rigid and flexible material that is collapsible and expandable.

Optionally, the rigid and flexible mesh 304 is returned to the open state by a force applied by spring 306.

Optionally, spring 306 is anchored at a first end to hollow rod 302, for example, anchored to a distal portion of a rigid rod 322 at an anchor point 324. Optionally, anchor 324 is substantially round, without sharp edges, so as not to inadvertently puncture the vein wall during the treatment.

Optionally, a second end of spring 306 is coupled to a second end of mesh 304.

Optionally, mesh 304 is compressed and/or expanded (shown as arrows 328) by related compression and/or expansion of spring 306 (shown as arrows 326).

Advantageously, the resiliency of spring 306 may allow mesh 304 to be compressed for delivery to vein segment 320, may allow mesh 304 to expand at vein segment 320, and/or may provide a counter force that allows mesh 304 to return to the irritation state after compression from spasm and/or collapse of segment 320.

In operation, catheter 300 is delivered to vein segment 320. Optionally, catheter 300 is delivered through a guiding outer sheath 330. Mesh 304 expands (e.g., self-expands) in vein segment 320. Expanding mesh 304 props open collapsed walls of vein segment 320. Mesh 304 irritates inner wall of vein segment 320, optionally triggering a spasm. The spasm applies a compressive force to mesh 304 and spring 306. Under the feedback from the force, spring 306 provides a mechanical counter-force to return mesh 304 to the expanded irritation state. The process of spring compression and the spring applying the counter-force is dynamic and iterative. For example, the vein segment may spasm, collapse and relax several times, and/or adjacent vein segments may each spasm as the vein is treated. Vein segments may collapse with different forces.

Optionally, rod 302 comprises one or more opening 332. Optionally, openings 332 are in fluid communication with a fluid source containing a sclerosant agent for injection into vein 320. Optionally, openings 332 are arranged to release the sclerosant agent (shown as arrows 334) within vein segment 320, optionally in proximity to the inner wall. Optionally, the released sclerosant agent, blood and/or other debris are removed through sheath 330 (shown as arrows 336).

Reference is now also made to FIG. 4, which is a schematic illustration of another vein treatment catheter 400, in accordance with embodiments of the present invention. Catheter 400 comprises bearing 426A to allow self-rotation of a mesh 404.

Optionally, mesh 404 self rotates by being dragged along the vein. Advantageously, the rotation does not require the use of a motor or other external power source.

Optionally, an irritation element is combined with a support element into interwoven mesh 404. Optionally, one or more of the support element are memory shape wires, such as an SMA wire 406, for allowing the expanding of mesh 404 so as to contact and irritate inner wall of vein segment 420. Optionally, one or more of the irritation element are mechanical irritating wires 404, for example coarse and/or jagged wires. Optionally, the irritation element is made from a resilient material with an elasticity coefficient adapted to scratch the inner wall without irritating tissue surrounding the inner wall.

Optionally, mesh 404 is substantially tubular, with tapered ends. Optionally, the tapered ends are coupled to a proximal end region of a rigid rod 422. The tapered ends are coupled to rod 442 so that rotational motion (shown by arrows 424) around rod 422 is allowed. For example, bearings 426A-B couple distal ends of mesh 404 to rod 422.

Optionally, bearing 426B is slidably coupled to rod 442 (motion shown by arrows 428). Optionally, sliding bearing 426B allows mesh 402 to change diameters, for example, during changes in state from expansion to contraction.

Advantageously, the ability of mesh 404 to rotate and/or the distal end of mesh 404 to slide may provide mesh 404 with the ability to navigate tortuous venous anatomy, while at the same time propping open the vein and/or irritating the vein.

Reference is now also made to FIG. 5, which is a schematic illustration of yet another vein treatment catheter 500, in accordance with embodiments of the present invention. Catheter 500 comprises a mesh 504 with drug 540. Optionally, the drug is irritating to the wall of vein segment 540, for example, the drug is a sclerosant agent.

Optionally, drug 540 is coated on mesh 504. Alternatively or additionally, drug 540 is impregnated within mesh 504. Alternatively or additionally, drug 540 is impregnated on another material, for example, a polymer. The polymer may coat mesh 504, may be interlaced with mesh 504, or may be inside mesh 504.

Optionally, drug 540 is delivered to vein segment 520 by direct contact of mesh 504 and/or the polymer coupled to mesh 504 with the inner wall. Alternatively or additionally, drug 540 leaks out into the blood in proximity to the inner wall, and diffuses into the venous wall through the blood.

Advantageously, the drug-mesh element may deliver mechanical and chemical irritation at the same time. Advantageously, the drug-mesh element may deliver chemical irritation directly to the inner wall.

Reference is now also made to FIG. 6, which is a schematic illustration of yet another vein treatment catheter 600, in accordance with embodiments of the present invention. Catheter 600 comprises a self-expanding mesh 604 with optional drug 640.

Optionally, mesh 604 is arranged to exert a self-expanding force that is strong enough to prop open vein segment 620. Alternatively or additionally, mesh 604 is arranged to exert a self-expanding force strong enough to return vein 620 to the open state against collapse and/or spasm.

Optionally, mesh 604 chemically irritates segment 620 using drug 640.

Optionally, mesh 604 does not mechanically irritate segment 620, so that without drug 640 mesh 604 alone would not trigger spasm. Advantageously, mesh 604 may reduce and/or prevent the risk of excessive mechanical damage, for example, vein perforation, deep scratches, and/or damage to surrounding tissue. Alternatively, mesh 604 mechanically irritates segment 620. Optionally, mesh 604 is arranged to exert a self expanding force strong enough to return mesh 604 to the irritating state.

Figure 7:
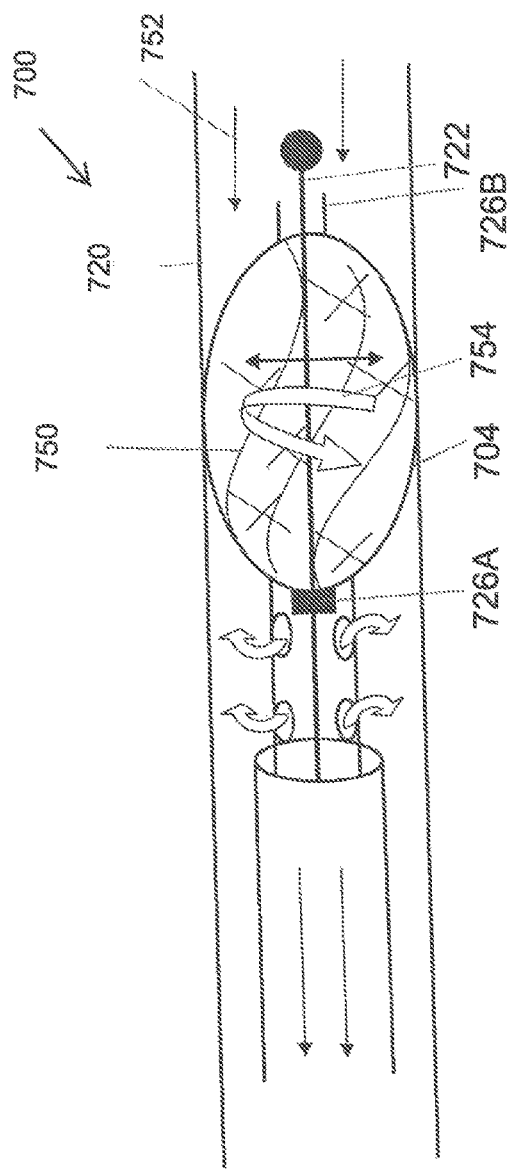
FIG. 7 is a schematic of yet another vein treatment catheter, in accordance with embodiments of the present invention.

Reference is now also made to FIG. 7, which is a schematic illustration of yet another vein treatment catheter 700, in accordance with embodiments of the present invention. Mesh 704 is coupled by coupling mechanism 726A-B so that mesh 704 is able to rotate around rod 722. Mesh 704 self rotates by being dragged along the vein. Advantageously, the rotation does not require the use of a motor or other external power source.

Mesh 704 comprises one or more helixes 750 arranged on the outer surface of mesh 704, for example, helixes 750 are formed from elevated parallel wires. Helixes 750 are arranged so that displacement of mesh 704 (e.g., proximally as shown by arrows 752) rotates mesh (shown by arrow 754).

Optionally, rotating mesh 704 irritates the entire circumference of the inner wall of vein segment 720. Optionally, the irritation is performed in a helical manner, for example, a single pin scratching the inner wall while being displaces tracks a helical pattern.

Advantageously, the rotating mesh 704 may form a better irritating coverage of the inner wall.

Figure 8:
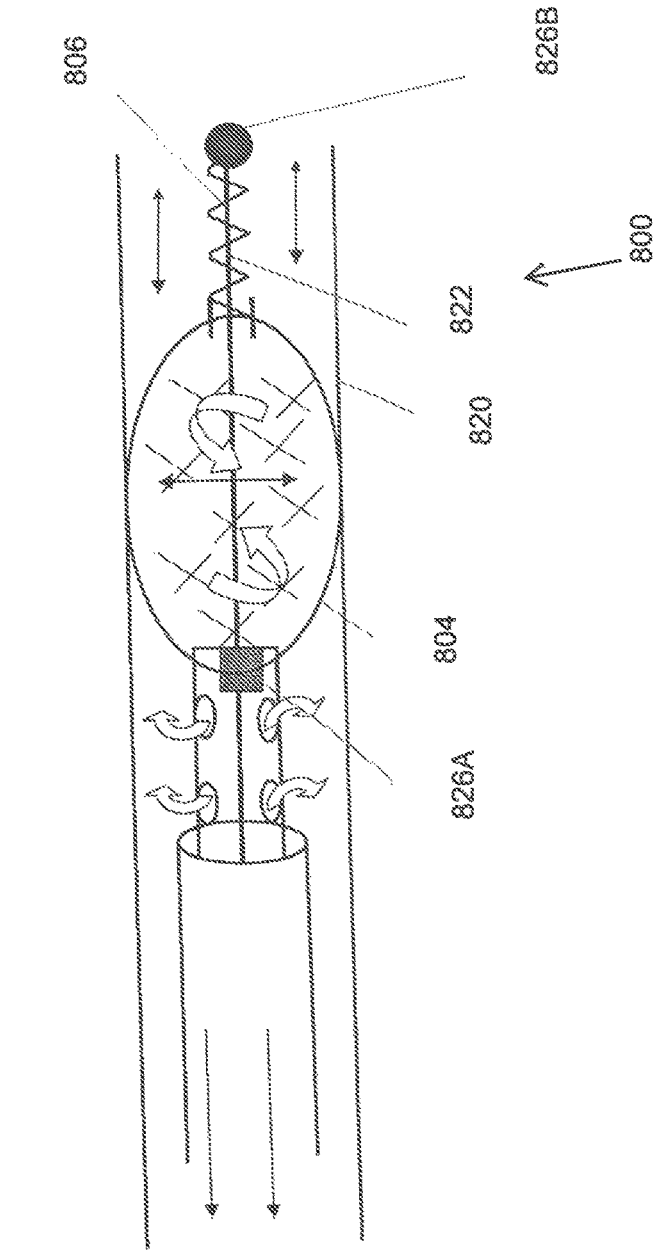
FIG. 8 is a schematic of yet another vein treatment catheter, in accordance with embodiments of the present invention.

Reference is now also made to FIG. 8, which is a schematic illustration of yet another vein treatment catheter 800, in accordance with embodiments of the present invention. Catheter 800 comprises mesh 804 arrange for self rotation and for a return to the expanded irritation state using a spring 806.

Mesh 804 is coupled to a rigid rod 822 at a first end by a bearing 826A allowing for rotational motion (e.g., similar to bearing 426A of FIG. 4). Mesh 804 is attached at a second end to spring 806 (e.g., similar to spring 306 of FIG. 3). Spring 806 is coupled to rod 822 using a second coupling mechanism, for example, a second bearing 826B, allowing for rotational motion of spring 806.

Advantageously, catheter 800 may return vein segment 820 to the propped open state, while navigating through tortuous anatomy.

Figure 9:
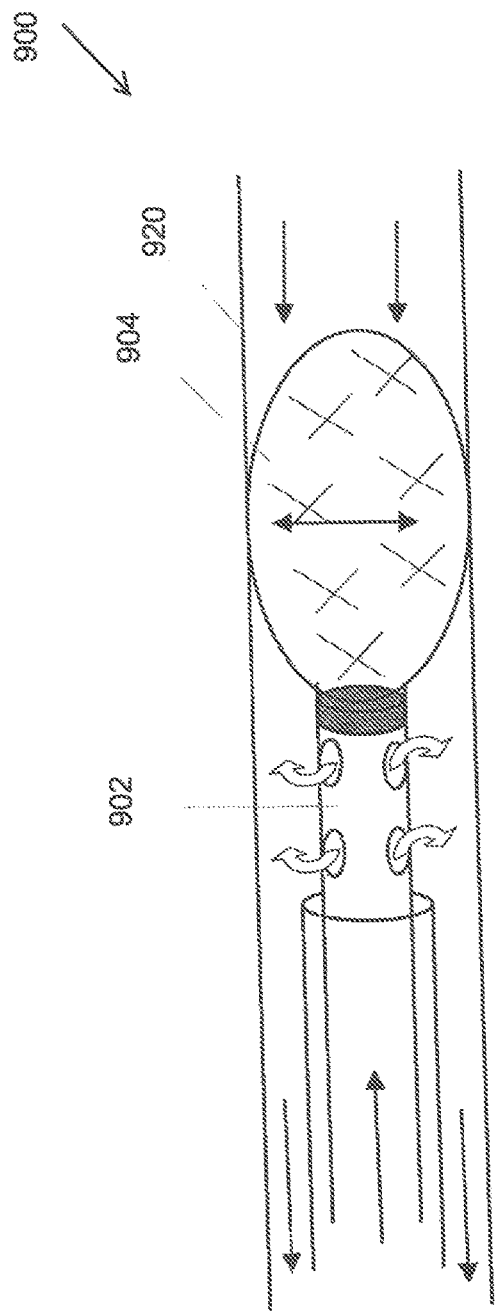
FIG. 9 is a schematic of yet another vein treatment catheter, in accordance with embodiments of the present invention.

Reference is now also made to FIG. 9, which is a schematic illustration of yet another vein treatment catheter 900, in accordance with embodiments of the present invention. Catheter 900 comprises mesh 904 made out of interwoven wires, interwoven mesh 904 having the properties of both being able to support and to irritate. Optionally, mesh 904 is coupled to tube 902 so that mesh 904 is not able to freely rotate around the longitudinal axis of tube 902. Advantageously, the secure attachment of mesh 904 to rob 902 may provide a stronger irritation to vein 920.

Figure 10:
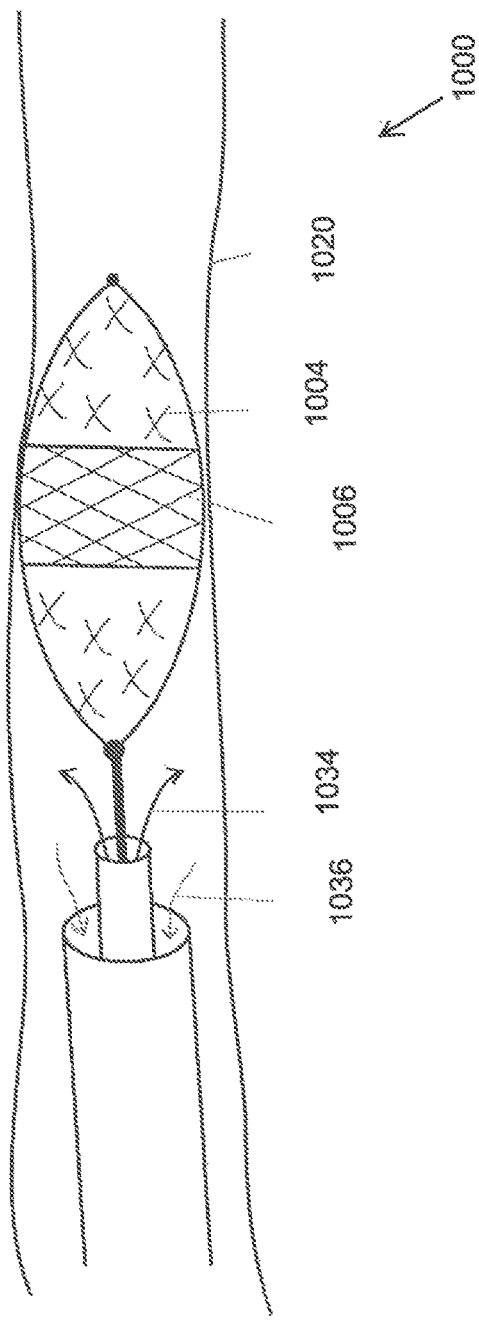
FIG. 10 is a schematic of yet another vein treatment catheter, in accordance with embodiments of the present invention.

Reference is now also made to FIG. 10, which is a schematic illustration of yet another vein treatment catheter 1000, in accordance with embodiments of the present invention. Catheter 1000 comprises an irritation element 1006 coupled to and/or arranged around the circumference of support element 1004 so that expansion of support element 1004 expands irritation element 1006. Expanded element 1006 contacts and/or irritates wall 1020. Irritation element 1006 is arranged, for example, along the outer surface of element 1004, interwoven within element 1004, along the inner surface of element 1004, and/or any other suitable arrangements or combinations thereof.

Catheter 1000 is comprised of a support element 1004. Optionally, support element 1004 is a tubular mesh having expandable and/or collapsible states. Optionally, support element 1004 is made from a resilient material with an elasticity coefficient adapted to contact the inner wall of vein 1020 without irritating tissue surrounding of the inner wall to trigger spasm or cause damage, for example, Nitinol wires without sharp edges.

Alternatively, support element 1004 is a balloon, for example, balloon 1604 as described with reference to FIG. 16.

Optionally, catheter 1000 is comprised of an irritation element 1006. Optionally, irritation element 1006 is a tubular mesh having expandable and/or collapsible states, for example, a ring. Optionally, irritation element 1006 is made from a flexible material that is unable to maintain the tubular structure without support, for example, a biocompatible polymer. Optionally, the flexible irritation element 1006 is made out of a material with an elasticity coefficient adapted to contact and irritate inner wall 1020 without causing clinical damage to deeper tissue layers or surrounding tissue structures.

Optionally, sclerosant infusion 1034 and optional removal 1036 are performed as part of the treatment, for example, as described hereinabove.

Advantageously, coupling of separate irritation and support elements may allow improved selection and/or design of each separate component according to the respective functions.

Figure 11:
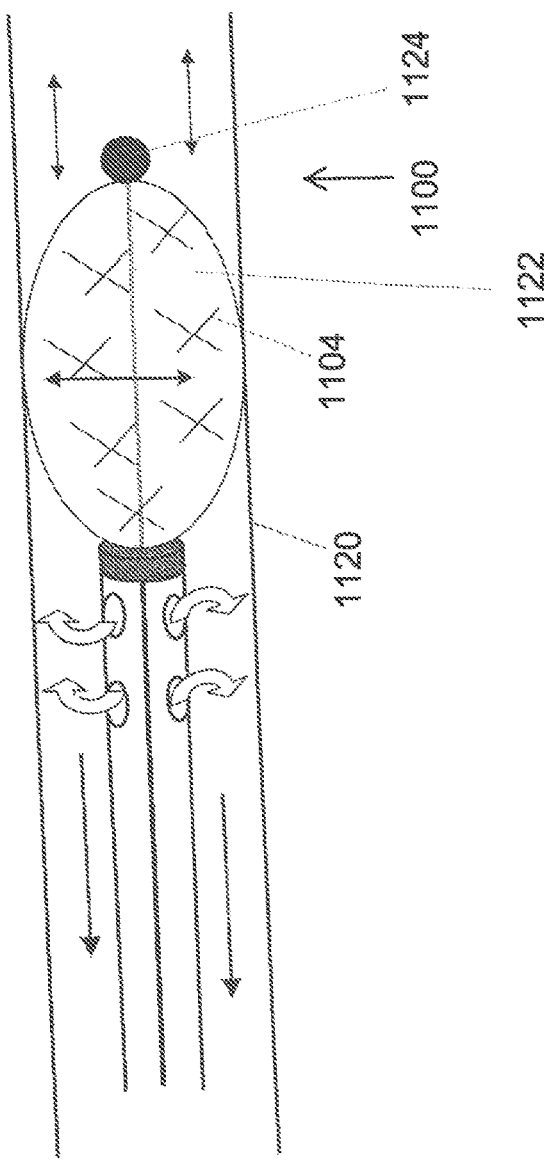
FIG. 11 is a schematic of yet another vein treatment catheter, in accordance with embodiments of the present invention.

Reference is now also made to FIG. 11, which is a schematic illustration of yet another vein treatment catheter 1100, in accordance with embodiments of the present invention. Catheter 1100 comprises mesh 1104 coupled to a rigid rod 1122, for example, at an anchor 1124. Optionally, distal or proximal displacement of rod 1122 (e.g., manually by an operator) expands or contracts mesh 1104.

Optionally, the support element component of interwoven mesh 1104 is not capable of supporting mesh 1104 to fully contact wall 1120. Alternatively or additionally, mesh 1104 is not made out of a self-expanding material.

Advantageously, manual control over expansion and contraction of mesh 1104 may allow for more flexible and/or less rigid materials to be used that may reduce risk of vascular damage. Advantageously, manual control may allow more flexibility for the operator in controlling the irritation.

Figure 12:
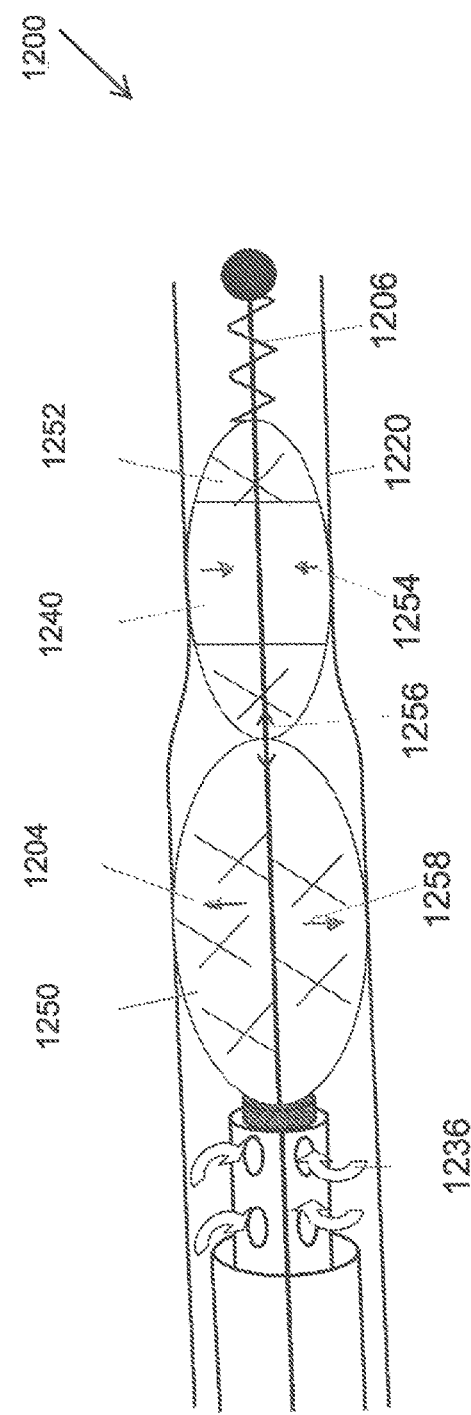
FIG. 12 is a schematic of yet another vein treatment catheter, in accordance with embodiments of the present invention.

Reference is now also made to FIG. 12, which is a schematic illustration of yet another vein treatment catheter 1200, in accordance with embodiments of the present invention. Catheter 1200 comprises mesh 1204 with a proximal portion 1250 and a distal portion 1252 arranged so that compressive forces applied to one portion are transferred to the adjacent portion, and converted into expansion forces of the adjacent portion.

Optionally, portions 1250 and 1252 are two separate meshes in mechanical contact with one another and/or are affixed to one another.

Compression forces are applied by collapse of vein walls 1220, such as a spasm. As shown vein segment has spasmed around portion 1252, exerting compressive forces (shown as arrows 1254). The compression forces are transferred to portion 1250 through the contact, neck or constriction (shown as arrows 1256). The compressive forces are transformed into expansion of portion 1250 (shown as arrows 1258). Without being bound to theory, mesh 1204 yields to maintain a constant internal volume, for example, like an elongated balloon filled with water so that compressing the balloon at one end expands the balloon at another location.

Optionally, catheter 1200 comprises of an expansion element 1206, for example a spring, as described with reference to element 306 of FIG. 3. Alternatively or additionally, mesh 1204 comprises the expansion element, for example, interwoven therein, as described hereinabove. Alternatively or additionally, mesh 1204 is manually expandable and collapsible, for example, comprising a rigid rod as described hereinabove.

Optionally, one portion (e.g., distal portion 1252) comprises a drug coating 1240 and/or is porous to release drugs from an interior thereof, for example, similar to coating 540 described with reference to FIG. 5 and/or similar to porous balloon described with reference to FIG. 16. Optionally, the other portion (e.g., proximal portion 1250) comprises mechanical irritating features as described hereinabove. Alternatively, both portions comprise drug coatings and/or drug eluting and/or mechanically irritating features.

Although mesh 1204 has been described with two portions, other numbers of additional portions are possible, so that compressive forces acting on one portion are transferred proximally and/or distally to adjacent portions.

Advantageously, instead of fully resisting the compressive forces exerted by the venous wall, some compression is allowed, with the compression transferred into adjacent expansion. Advantageously, the mesh may be made from a softer and/or more flexible material that may reduce inadvertent tissue damage, while still maintaining the ability to resist compressive forces of the venous wall.

Optionally, sclerosant infusion and optional removal 1236 are performed as part of the treatment, for example, as described hereinabove.

Reference is now also made to FIG. 13, which is a schematic illustration of yet another vein treatment catheter 1300, in accordance with embodiments of the present invention. Catheter 1300 comprises mesh 1304 with portions 1350 and 1352 as part of a single mesh with a neck or constriction 1360 (e.g., a slidable rigid ring around mesh 1204) between the two portions.

Optionally, constriction 1360 allows for distal and/or proximal displacement of mesh 1304 (shown by arrows 1362) so that compression of one portion is transferred and converted into expansion of the adjacent portion.

Optionally, mesh 1304 is supported by the spring as described with reference to FIG. 12. Alternatively or additionally, mesh 1304 is self-expandable, as described hereinabove. Alternatively or additionally, mesh 1304 is manually expandable, for example, by using a rigid pushrod 1322 as described hereinabove.

Reference is now also made to FIG. 14, which is a schematic illustration of yet another vein treatment catheter 1400, in accordance with embodiments of the present invention. Catheter 1400 comprises a helical shaped element 1406 with at least one bend 1470 propping open and/or returning vein segment 1420 to the open state. Helix 1406 is arranged to transition between an expanded irritating state, and a non-irritating state.

Optionally, helical element 1406 comprises of a rigid rod 1472 mechanically coupled to a distal end portion thereof. Proximal or distal displacement of rod 1472 stretches or compresses helical element 1406 so that the outer diameter of helical element 1406 is increased or decreased, and element 1406 is iteratively transitioned between the irritating and non-irritating states. Advantageously, manipulation of rod 1472 may be used to iteratively return helical element 1406 to the irritation state against the dynamic feedback of the vein segment walls pushing in on helical element 1406.

Rod 1472 may be manipulate manually by the user, and/or automatically manipulated by one or more support elements as described herein.

Optionally, rod 1472 and/or the support element are arranged to apply a mechanical force from the distal end portion of rod 1472 to iteratively return helix 1406 to the expanded irritation state in response to dynamic feedback of the vein segment walls pressing against helix 1406 to force helix 1406 to the non-irritation state.

Optionally, helical element 1406 is arranged around a central axis, for example, rigid rod 1472. Optionally, helical element 1706 contacts vein 1420 at bends 1470 that are spaced around the circumference of vein 1420 so that vein 1420 is propped open.

Helical element 1406 may be other shapes, for example, several adjacent Ws, M shaped, a sinusoid, a spiral, or other suitable shapes.

Optionally, helical element 1406 comprises irritation elements 1404, at least at bends 1470, for example, irritation features on the surface thereof.

Optionally, helical element 1406 is a hollow tube. Optionally, helical element 1406 contains one or more openings 1432 for releasing a sclerosant agent 1434 in proximity to inner walls 1420. Optionally, openings 1432 are located away from irritation elements 1404 of bends 1470.

Optionally, removal of waste 1436 is performed through an outer sheath 1430.

Optionally, helical element 1406 is made from a self-expanding material, for example, Nitinol. Alternatively or additionally, helical is made from a flexible material that requires expansion, for example, a biocompatible polyurethane.

Reference is now also made to FIGS. 15A-B, which are schematic illustrations of yet another vein treatment catheter 1500, in accordance with embodiments of the present invention. Catheter comprises a tube 1502 with one or more openings 1532 arranged to release a sclerosing substance 1534 within the interior of mesh 1504. FIG. 15A shows delivery of a mesh 1504 in a compressed state. FIG. 15B shows delivery of mesh 1504 in the expanded state. Optionally, mesh 1504 is made from a self-expanding arranged material.

Optionally, mesh 1504 props open vein segment 1520.

Optionally, mesh 1504 is tubular. Optionally, tubular mesh 1504 surrounds a tube 1502.

Optionally, substance 1534 is released in proximity to inner walls of vein segment 1520. Optionally, substance 1534 exits through gaps formed by wires of mesh 1504. Optionally, substance 1534 contacts the inner wall.

Optionally, mesh 1504 is formed out of tightly packed wires, so that the gaps between the wires are formed when mesh 1504 expands to contact the inner wall.

Optionally, mesh 1504 is arranged so that the gaps are only or mostly or largely formed at the regions where mesh 1504 contacts the inner wall. Advantageously, the sclerosant agent may selectively leak out of mesh directly into the wall.

Optionally, mesh 1504 mechanically irritates vein segment 1520. Alternatively, mesh 1504 is made out of a material that is flexible and/or smooth so that mesh 1504 props open vein segment 1520 without irritation.

Advantageously, releasing the sclerosant within mesh 1504 helps ensure that the inner vein wall is chemically irritated, with or without mechanical irritation.

Reference is now also made to FIG. 16, which is a schematic illustration of yet another vein treatment catheter 1600, in accordance with embodiments of the present invention. Catheter 1600 comprises an elastic expandable element, such as a balloon 1604.

Optionally, balloon 1604 is sized with a diameter larger than the resting diameter of the target vein segment. Optionally, balloon 1604 is expanded to a size larger than the resting diameter of the vein so that the inner vein wall 1620 is damaged by the expansion. Optionally, the vein is stretched beyond the elastic limit of the inner wall.

Optionally, the vein segment wall is stretched beyond the resting diameter so that the inner wall is damaged without clinical damage to surrounding tissues. Alternatively, instead of balloon 1604, a mesh (e.g., as described herein) is expanded to over-stretch and damage the inner wall.

Optionally, when in the expanded state, balloon 1604 props open vein segment 1620.

Optionally, balloon 1604 is expanded by injection of sclerosant agent 1634 into the interior of balloon 1604, for example, by a health practitioner from outside the body of the patient. Alternatively or additionally, balloon 1604 is expanded by injection of other fluids, for example, saline.

Optionally, balloon 1604 is made out of a porous material so that sclerosant agent 1634 leaks out of balloon 1604 (shown as arrows 1660). Leaked sclerosant 1660 contacts and chemically irritates inner wall 1620.

Alternatively or additionally, balloon 1604 is coated with the sclerosant material. The sclerosant material may be delivered to inner wall 1620 upon contact by the surface of balloon 1604 with inner wall 1620, and/or the sclerosant material may elute from the surface of balloon 1604 into the blood and then to inner wall 1620 (show as arrows 1660).

Alternatively or additionally, balloon 1604 provides support for an irritation element, for example, irritation element 1006 of FIG. 10. Alternatively or additionally, balloon 1604 serves as the irritation element, and the iterative return to the expanded irritating state of balloon 1604 is provided by one or more support elements as described herein.

Reference is now also made to FIG. 17, which is a schematic illustration of yet another vein treatment catheter 1700, in accordance with embodiments of the present invention. Catheter 1700 comprises one or more arch shaped wires 1704 to prop open walls of a vein segment.

Optionally, distal ends of wires 1704 meet at a distal anchor 1750, and proximal ends of wires 1704 meet at a proximal anchor 1752. Optionally, wires 1704 are arranged around a longitudinal axis of catheter 1700.

Optionally, one or more irritation wires 1706 are coupled to arch wires 1704 so that wires 1704 support wires 1706 to contact the inner vein wall. Optionally, irritation wires 1706 mechanically irritate the inner vein wall upon contact and/or upon displacement against the wall.

Optionally, irritation wires 1706 are arranged in a helical pattern around support wires 1704.

Optionally, wires 1704 and/or 1706 are arranged for collapse into a collapsible state for delivery through a guiding sheath. Optionally, wires 1704 and/or 1706 are arranged for expansion from the collapsible state into an expanded state.

Optionally, wires 1704 and/or 1706 are disposed at a distal portion of a rigid rod 1722 that is able to navigate through the blood vessels to reach the target vein segment.

Advantageously, catheter 1700 may be compressed into a small delivery diameter, by lining up the helixes one within the other.

Reference is now also made to FIG. 18A, which is a schematic illustration of yet another vein treatment catheter 1800 comprising one or more wires arranged as petals 1804, in accordance with embodiments of the present invention. Reference is now also made to FIG. 18B, which is a face-on view of catheter 1800.

Optionally, petals 1804 are arranged circumferentially around, and coupled together, at an anchor 1850 point. Optionally, anchor 1850 is located at a distal portion of a rigid rod 1822.

Optionally, petals 1804 prop open vein segment 1820. Alternatively or additionally, petals 1804 mechanically irritate vein segment 1820.

Optionally, petals 1804 are arranged with an inner support wire, and an outer irritation wire, for example, wires 1704 and 1706 of FIG. 17.

Optionally, petals 1804 are arranged to be compressible for delivery through sheath 1830 and for expansion to contact walls of vein segment 1820.

Optionally, petals 1804 are arranged in a distal tilt from anchor 1850. Optionally, each petal 1804 is not coupled to the adjacent petal. Optionally, the angle of the tilt of each petal 1804 is independent. Alternatively, petals 1804 are at least partially coupled to adjacent petals 1804. Optionally, all or most petals 1804 tilt together.

Optionally, a sclerosing agent 1834 may be injected during the treatment.

Advantageously, the distal tilt of the pedals may make it easier to proximally displace the pedals through the vein, while maintaining contact with the vein wall.

Advantageously, the independence of each pedal may allow the pedals to conform to the tortuous venous anatomy, while propping open the vein segment and/or irritating the inner wall.

Reference is now also made to FIG. 19A, which is a schematic illustration of yet another vein treatment catheter 1900 comprising one or more fins 1904, in accordance with embodiments of the present invention. Reference is now also made to FIG. 19B, which is an elevated view of catheter 1900 in the vein.

Fins 1904 are arranged to prop open vein segment 1920.

Optionally, fins 1904 are arranged in a spiral around a hollow tube 1922.

Optionally, fins 1904 are resilient and/or biased to expand and increase the spiral diameter when located in vein segment 1920, from a smaller spiral diameter when being delivered through sheath 1930.

Optionally, edges of fins 1904 prop open vein segment 1920 without irritating the inner wall. Alternatively, edges of fins 1904 irritate the inner wall during contact.

Optionally, fins 1904 comprise one or more openings 1932 in fluid communication with hollow tube 1922. Optionally, openings 1932 are used to remove an injected sclerosant agent (fluid and/or foam) from within the vein segment (shown as arrow 1950). Alternatively or additionally, openings 1932 are used to inject the sclerosant agent into the vein segment.

Optionally, tube 1922 comprises one or more openings 1952 for injection of the sclerosant agent (shown as arrows 1954) and/or removal of the agent.

Optionally, tube 1922 is divided into two or more channels, one channel for sclerosant agent delivery and another channel for sclerosant agent removal. For example, the sclerosant agent is injected through openings 1952 and at the same time the agent is removed from the interior of the vein through openings 1932. Alternatively, tube 1922 is a single channel.

Optionally, catheter 1900 comprises one or more additional elements 1906, for example, a tubular mesh, a balloon, or other structures as described herein. Optionally, element 1906 mechanically irritates the inner wall, chemically irritates the inner wall and/or props open the inner wall. Optionally, element 1906 is located proximally and/or distally relative to fins 1904.

Advantageously, catheter 1900 provides two elements which may have a combined synergistic effect of improved irritation of the vein wall.

It is expected that during the life of a patent maturing from this application many relevant vessel irritation devices will be developed and the scope of the term vessel irritation device is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An endovascular catheter for vein ablation comprising: an elongated rod having a proximal end and a distal end portion, the elongated rod being sized for insertion into a vein; at least one irritation element coupled to the distal end portion of the elongated rod, the at least one irritation element having an expanded irritation state for contacting an inner wall segment of the vein to irritate the inner wall segment of the vein to trigger spasm of the inner wall segment of the vein and a non-irritation state, the at least one irritation element arranged for iterative changes between the expanded irritation state and the non-irritation state; and a first bearing coupling a first end of the at least one irritation element to the elongated rod and mounted to slidably move along the elongated rod for allowing the at least one irritation element to change diameter when moving from the expanded irritation state to the non-irritation state in response to dynamic feedback from the inner wall segment of the vein pressing against the at least one irritation element;

a second bearing coupling a second end of the at least one irritation element to the elongated rod; wherein the first and second bearings couple the at least one irritation element to the distal end portion to provide self-rotational motion of the at least one irritation element along a longitudinal axis of the elongated rod independently of the elongated rod when the vein applies forces to the at least one irritation element as the at least one irritation element is dragged inside the vein.

2. The endovascular catheter of claim 1, wherein the at least one irritation element comprises a flexible mesh woven from a first wire made of a shape memory material and a second flexible wire arranged for contacting and irritating the inner wall segment of the vein.

3. The endovascular catheter of claim 1, further comprising an anchor coupled to the distal end portion of the elongated rod, the anchor configured to be biased to return the at least one irritation element to the expanded irritation state.

4. The endovascular catheter of claim 1, wherein the at least one irritation element is made from a resilient material with an elasticity coefficient adapted to scratch the inner wall segment of the vein without irritating tissue surrounding, the inner wall segment of the vein.

5. The endovascular catheter of claim 1, further comprising, a fluid insertion channel having one or more first openings at the distal end portion, the one or more first openings arranged for releasing a medical substance in near proximity to the inner wall segment of the vein.

6. The endovascular catheter of claim 5, further comprising, a fluid removal channel having one or more second openings at the distal end portion, the one or more second openings arranged for removing fluid and debris from the inner wall segment of the vein.

* * * * *